US008808225B2

(12) United States Patent
Prausnitz et al.

(10) Patent No.: US 8,808,225 B2
(45) Date of Patent: *Aug. 19, 2014

(54) METHODS AND DEVICES FOR DRUG DELIVERY TO OCULAR TISSUE USING MICRONEEDLE

(75) Inventors: Mark R. Prausnitz, Atlanta, GA (US); Henry F. Edelhauser, Atlanta, GA (US); Samirkumar Rajnikant Patel, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/447,246

(22) Filed: Apr. 15, 2012

(65) Prior Publication Data

US 2012/0226260 A1 Sep. 6, 2012

Related U.S. Application Data

(63) Continuation of application No. 12/767,768, filed on Apr. 26, 2010, now Pat. No. 8,197,435, which is a continuation-in-part of application No. 11/743,535, filed on May 2, 2007, now Pat. No. 7,918,814.

(60) Provisional application No. 60/746,237, filed on May 2, 2006, provisional application No. 61/172,409, filed on Apr. 24, 2009.

(51) Int. Cl.
*A61N 1/30* (2006.01)
*A61F 9/00* (2006.01)

(52) U.S. Cl.
CPC .................................... *A61F 9/0017* (2013.01)
USPC .......................................................... 604/19

(58) Field of Classification Search
USPC .......................................... 604/19, 22, 28, 44
See application file for complete search history.

(56) References Cited

U.S. PATENT DOCUMENTS

| 4,826,871 A | 5/1989 | Gressel et al. |
| 4,966,773 A | 10/1990 | Gressel et al. |

(Continued)

FOREIGN PATENT DOCUMENTS

| WO | 00/07530 | 2/2000 |
| WO | 00/07565 | 2/2000 |

(Continued)

OTHER PUBLICATIONS

Beer et al., Photographic Evidence of Vitreous Wicks After Intravitreal Injections, Retina Today 2(2): 24-29 (2007).
Edwards & Prausnitz, Fiber matrix model of sclera and corneal stroma for drug delivery to the eye, AIChE Journal 44(1): 21425 (1998).
Jiang et al. Measurement and Prediction of Lateral Diffusion within Human Sclera, Investigative Ophthalmology & Visual Science 47(7): 3011-3016 (2006).
Jiang et al. Coated Microneedles for Drug Delivery to the Eye, Investigative Ophthalmology & Visual Science 48(9): 4038-4043 (2007).
McAllister et al. Microfabricated needles for transdermal delivery of macromolecules and nanoparticles: Fabrication methods and transport studies, Proc. Nat'l Acad. Sci USA 00(24): 13755-60 (2003).
Wang et al. Minimally Invasive Extraction of Dermal Interstitial Fluid for Glucose Monitoring Using Microneedles, Diabetes Technology & Therapeutics 7(1): 131-141 (2005).

(Continued)

*Primary Examiner* — Nicholas Lucchesi
*Assistant Examiner* — Pritesh Patel
(74) *Attorney, Agent, or Firm* — Sutherland Asbill & Brennan LLP

(57) ABSTRACT

Methods and devices are provided for targeted administration of a drug to a patient's eye. In one embodiment, the method includes inserting a hollow microneedle into the sclera of the eye at an insertion site and infusing a fluid drug formulation through the inserted microneedle and into the suprachoroidal space of the eye, wherein the infused fluid drug formulation flows within the suprachoroidal space away from the insertion site during the infusion. The fluid drug formulation may flow circumferentially toward the retinochoroidal tissue, macula, and optic nerve in the posterior segment of the eye.

39 Claims, 19 Drawing Sheets

(56) References Cited

U.S. PATENT DOCUMENTS

| | | | |
|---|---|---|---|
| 5,364,374 | A | 11/1994 | Morrison et al. |
| 5,547,467 | A | 8/1996 | Pliquett et al. |
| 5,667,491 | A | 9/1997 | Pliquett et al. |
| 5,911,223 | A | 6/1999 | Weaver et al. |
| 6,280,470 | B1 | 8/2001 | Peyman |
| 6,299,603 | B1 | 10/2001 | Hecker et al. |
| 6,309,347 | B1 | 10/2001 | Takahashi et al. |
| 6,319,240 | B1 | 11/2001 | Beck |
| 6,334,856 | B1 | 1/2002 | Allen et al. |
| 6,378,526 | B1 | 4/2002 | Bowman et al. |
| 6,397,849 | B1 | 6/2002 | Bowman et al. |
| 6,503,231 | B1 | 1/2003 | Prausnitz et al. |
| 6,524,581 | B1 | 2/2003 | Adamis et al. |
| 6,611,707 | B1 | 8/2003 | Prausnitz |
| 6,743,211 | B1 | 6/2004 | Prausnitz et al. |
| 6,773,916 | B1 | 8/2004 | Thiel et al. |
| 7,207,965 | B2 | 4/2007 | Simon |
| 7,207,980 | B2 | 4/2007 | Christian et al. |
| 7,211,062 | B2 | 5/2007 | Kwon |
| 7,226,439 | B2 | 6/2007 | Prausnitz et al. |
| 7,722,581 | B2 | 5/2010 | Peyman |
| 7,914,803 | B2 | 3/2011 | Chowhan et al. |
| 7,918,814 | B2 * | 4/2011 | Prausnitz et al. ............... 604/19 |
| 7,918,874 | B2 | 4/2011 | Siegal |
| 7,947,660 | B2 | 5/2011 | Clark et al. |
| 8,172,830 | B2 | 5/2012 | Christian et al. |
| 8,173,617 | B2 | 5/2012 | Clark et al. |
| 8,197,435 | B2 * | 6/2012 | Prausnitz et al. ............... 604/19 |
| 2002/0082527 | A1 | 6/2002 | Liu et al. |
| 2002/0082543 | A1 | 6/2002 | Park et al. |
| 2003/0083645 | A1 | 5/2003 | Angel et al. |
| 2004/0106904 | A1 | 6/2004 | Gonnelli et al. |
| 2004/0199130 | A1 | 10/2004 | Chomenky et al. |
| 2004/0265365 | A1 | 12/2004 | Daddona et al. |
| 2005/0137525 | A1 | 6/2005 | Wang et al. |
| 2005/0209565 | A1 | 9/2005 | Yuzhakov et al. |
| 2006/0013859 | A1 | 1/2006 | Yamada et al. |
| 2006/0036318 | A1 | 2/2006 | Foulkes |
| 2006/0084942 | A1 | 4/2006 | Kim et al. |
| 2006/0086689 | A1 | 4/2006 | Raju |
| 2006/0178614 | A1 | 8/2006 | Nemati |
| 2006/0189608 | A1 | 8/2006 | Bingaman |
| 2007/0073197 | A1 | 3/2007 | Prausnitz et al. |
| 2007/0082841 | A1 | 4/2007 | Higuchi et al. |
| 2007/0093877 | A1 | 4/2007 | Beecham et al. |
| 2007/0202186 | A1 | 8/2007 | Yamamoto et al. |
| 2008/0131484 | A1 | 6/2008 | Robinson et al. |
| 2008/0228127 | A1 | 9/2008 | Burns et al. |
| 2009/0081277 | A1 | 3/2009 | Robinson et al. |
| 2010/0015158 | A1 | 1/2010 | Robinson et al. |
| 2010/0074957 | A1 | 3/2010 | Robinson et al. |
| 2010/0173866 | A1 | 7/2010 | Conston et al. |
| 2011/0112546 | A1 | 5/2011 | Juan et al. |
| 2011/0238075 | A1 | 9/2011 | Clauson et al. |
| 2012/0004245 | A1 | 1/2012 | May et al. |
| 2012/0035524 | A1 | 2/2012 | Silvestrini |
| 2012/0123437 | A1 | 5/2012 | Horvath et al. |
| 2012/0123440 | A1 | 5/2012 | Horvath et al. |
| 2012/0165723 | A1 | 6/2012 | Horvath et al. |
| 2012/0271272 | A1 | 10/2012 | Hammack et al. |
| 2013/0211335 | A1 | 8/2013 | Paques et al. |

FOREIGN PATENT DOCUMENTS

| | | |
|---|---|---|
| WO | 03/024507 | 3/2003 |
| WO | 2006/004595 | 1/2006 |
| WO | 2006058189 A2 | 6/2006 |
| WO | 2006/128034 | 11/2006 |
| WO | 2006/138719 | 12/2006 |
| WO | 2007/100745 | 9/2007 |

OTHER PUBLICATIONS

Olsen, et al., American J. Opthamology 142(5): 777-87 (Nov. 2006).

International Search Report and Written Opinion for PCT/US2007/068055 dated Nov. 7, 2007.

Berglin, et al., "Tracing of Suprachoroidally Microneedle Injected labeled Drugs and Microbeads in Human, Pig and Rabbit Tissue Using Liquid Nitrogen Snap-Freeze Thaw and Lypholization," Invest Ophthalmol Vis Sci 2010; 51: E-Abstract 5330.

Choy, et al., "Mucoadhesive microdiscs engineered for ophthalmic drug delivery: effect of particle geometry and fomulation on preocular residence time," Investigative Ophthalmology & Visual Science 49: 4808-4815 (Nov. 2008).

Einmahl, et al., "Evaluation of a novel biomaterial in the suprachoroidal space of the rabbit eye," Investigative Ophthalmology & Visual Science 43: 1533-1539 (May 2002).

Jiang, et al., "Intrascleral drug delivery to the eye using hollow microneedles," Pharmaceutical Research 26: 395-403 (Feb. 2009).

Lee, et al., "Drug delivery through the sclera: effects of thickness, hydration and sustained release systems," Experimental Eye Research 78: 599-607 (Mar. 2004).

Olsen, "Drug Delivery to the Suprachoroidal Space Shows Promise," Retina Today (Mar./Apr. 2007).

Patel, et al., "Suprachoroidal Drug Delivery Using Microneedles," Invest Ophthalmol Vis Sci 2008; 49: E-Abstract 5006.

Patel, et al., "Drug Binding to Sclera," Invest Ophthalmol Vis Sci 2009; 50 E-Abstract 5968.

Patel, et al "Intraocular Pharmacokinetics of Suprachoroidal Drug Delivery Administered Using Hollow Microneedles," Invest Ophthalmol Vis Sci 2010; 51: E-Abstract 3796.

Prausnitz, et al., "Permeability of cornea, sclera and conjunctiva: A literature analysis for drug delivery to the eye," Journal of Pharmaceutical Sciences 87:1479-88 (Dec. 1998).

Prausnitz, et al., "Measurement and prediction of transient transport across sclera for drug delivery to the eye," Industrial and Engineering Chemistry Research 37: 2903-07 (Dec. 1998).

Prausnitz, "Microneedles for Ocular Drug Delivery", Retina Today, Mar./Apr. 2007, p. 39.

Jason-Jiang, "Measurement and Prediction of Lateral Diffusion within Human Sclera", Investigative Ophthalmology & Visual Science—Jul. 2006 vol. 47 No. 7, pp. 3011-3016.

Rowe-Rendleman, "Prophylactic Intra-Scleral Injection of Steroid Compounds in Rabbit Model of Retinal Neovascularization", Invest Ophthalmol Vis. Sci. 2002:43:E-Abstract 3872, ARVO.

Hanekamp, "Inhibition of Corneal and Retinal Angiogenesis by Organic Integrin Antagonists After Intrascleral or Intravitreal Drug Delivery", Invest Ophthalmol Vis. Sci. 2002:43: E-Abstract 3710. ARVO.

Shuler Jr., "Scleral Permeability of a Small, Single-Stranded Oligonucleotide", Journal of Ocular Pharmacology and Therapeutics—20(2):159 (2004).

* cited by examiner

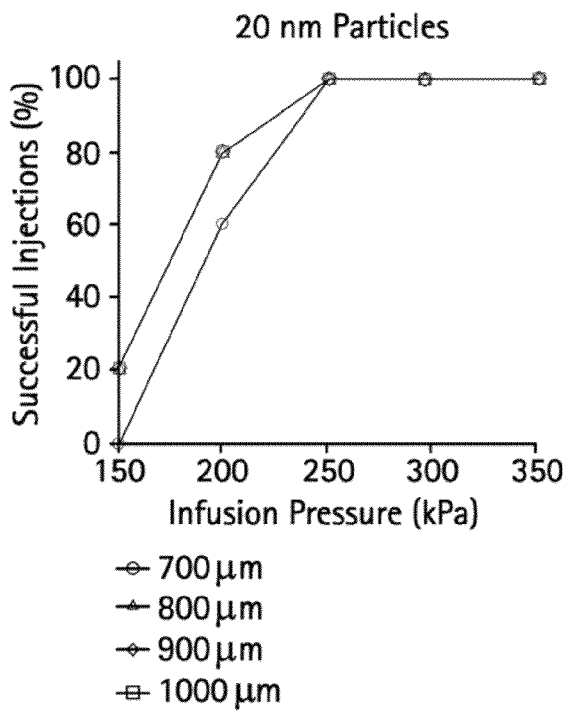
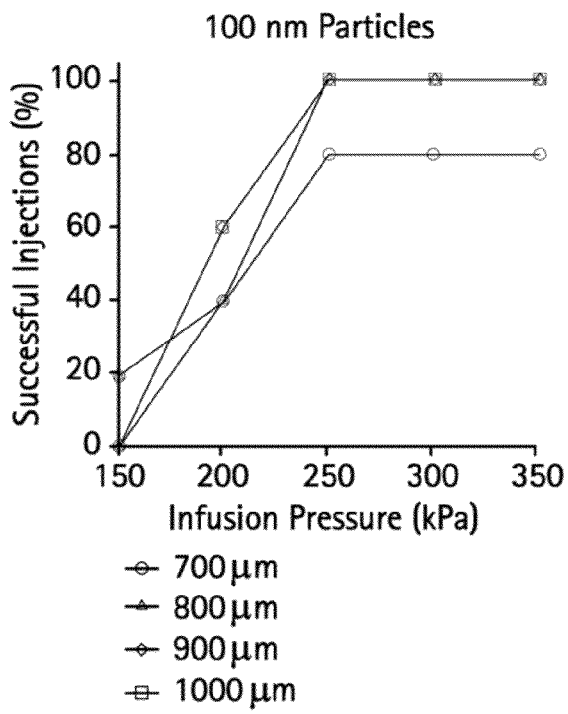
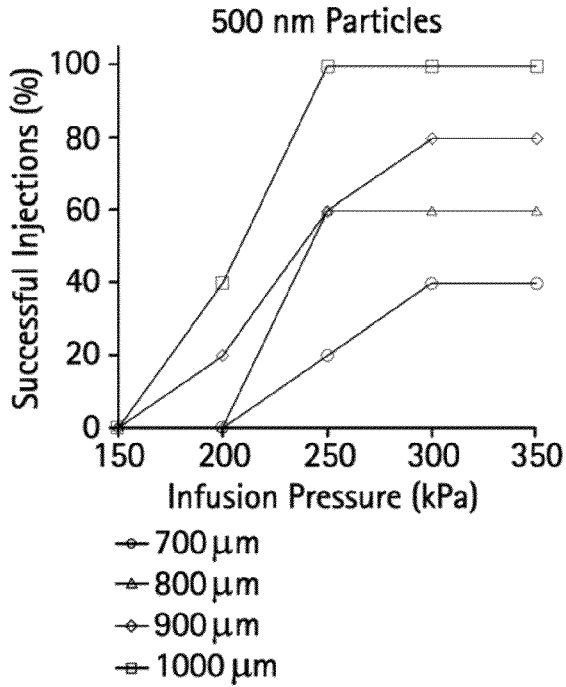
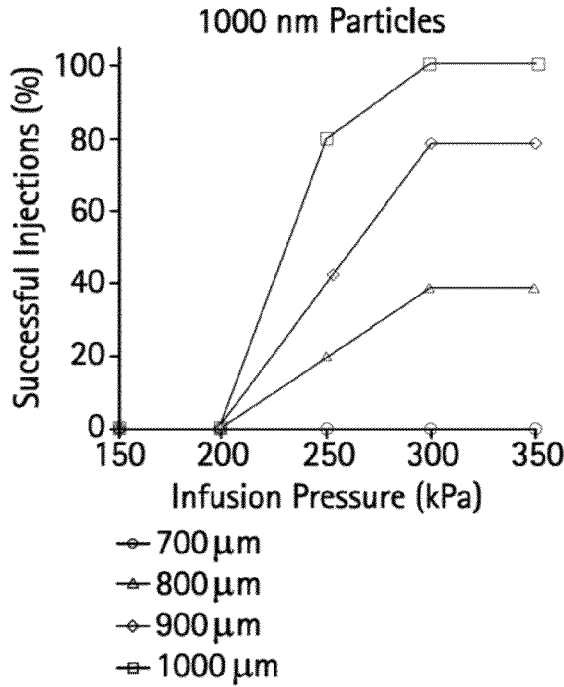

18 mmHg IOP 36 mmHg IOP

SCS Fluorescein Injection

METHODS AND DEVICES FOR DRUG DELIVERY TO OCULAR TISSUE USING MICRONEEDLE

CROSS REFERENCE TO RELATED APPLICATIONS

This application is a continuation of U.S. application Ser. No. 12/767,768, filed Apr. 26, 2010, which is a continuation-in-part of U.S. application Ser. No. 11/743,535, filed May 2, 2007, which claims benefit of U.S. Provisional Application No. 60/746,237, filed May 2, 2006. Benefit is also claimed to U.S. Provisional Application No. 61/172,409, filed Apr. 24, 2009. These applications are incorporated herein by reference.

STATEMENT REGARDING FEDERALLY SPONSORED RESEARCH OR DEVELOPMENT

This invention was made with U.S. government support under Contract No. 8 RO1 EB00260-03 and Contract No. R24EY017045-01, which were awarded by the National Institute of Health. The U.S. government has certain rights in the invention.

BACKGROUND OF THE INVENTION

This invention is generally in the field of ophthalmic therapies, and more particularly to the use of a microneedle for infusion of a fluid drug formulation into ocular tissues for targeted, local drug delivery.

The delivery of drug to the eye is extremely difficult, particularly delivery of macromolecules and delivery to the back of the eye. Many inflammatory and proliferative diseases in the posterior region of the eye require long term pharmacological treatment. Examples of such diseases include macular degeneration, diabetic retinopathy, and uveitis. It is difficult to deliver effective doses of drug to the back of the eye using conventional delivery methods such as topical application, which has poor efficacy, and systemic administration, which often causes significant side effects. (Geroski & Edelhauser, *Invest. Ophthalmol. Vis. Sci.* 41:961-64 (2000)). For example, while eye drops are useful in treating conditions affecting the exterior surface of the eye or tissues at the front of the eye, the eye drops cannot significantly penetrate to the back of the eye, as may be required for the treatment of various retinal diseases.

Direct injection into the eye, using conventional needles and syringes is often effective, but requires professional training and raises concerns about safety (Maurice, J. *Ocul. Pharmacol. Ther.* 17:393-401 (2001)). It also would be desirable to be able to minimize the number and/or frequency of eye injection treatments needed to deliver therapeutically effective amounts of drug to the ocular tissue sites that need it.

The suprachoroidal space of the eye has been studied, and its cannulation described as a possible route for drug delivery. See, e.g., Olsen, et al., *American J. Ophthalmology* 142(5): 777-87 (November 2006); PCT Patent Application Publication No. WO 2007/100745 to Iscience Interventional Corporation.

It therefore would be desirable to provide better, safer, more effective techniques for the direct delivery of therapeutic agents to eye tissues. It also would be desirable to provide devices useful in such techniques which can be relatively inexpensive to produce and use. It further would be desirable to provide methods for pinpoint delivery of drug to sclera, choroidal, uveal, macular, ciliary, vitreous and retinal tissues.

SUMMARY OF THE INVENTION

Methods and devices are provided for administering a drug to an eye of a patient. The methods may be used, for example, in the treatment of uveitis, glaucoma, diabetic macular edema, age-related macular degeneration, or cytomegalovirus retinitis. In one aspect, the method includes inserting a hollow microneedle into the sclera of the eye at an insertion site, the microneedle having a tip end with an opening; and infusing over a period of time a fluid drug formulation, which comprises a drug, through the inserted microneedle and into the suprachoroidal space of the eye, wherein during the period the infused drug formulation flows within the suprachoroidal space away from the insertion site.

BRIEF DESCRIPTION OF THE DRAWINGS

FIGS. 11A, 11B, 11C, and 11D are graphs showing the effect of infusion pressure and microneedle length on the success rate of suprachoroidal delivery of 20 nm particles (11A), 100 nm particles (11B), 500 nm particles (11C), and 1000 nm particles (11D) into pig eyes.

DETAILED DESCRIPTION OF PREFERRED EMBODIMENTS

Figure 1A:
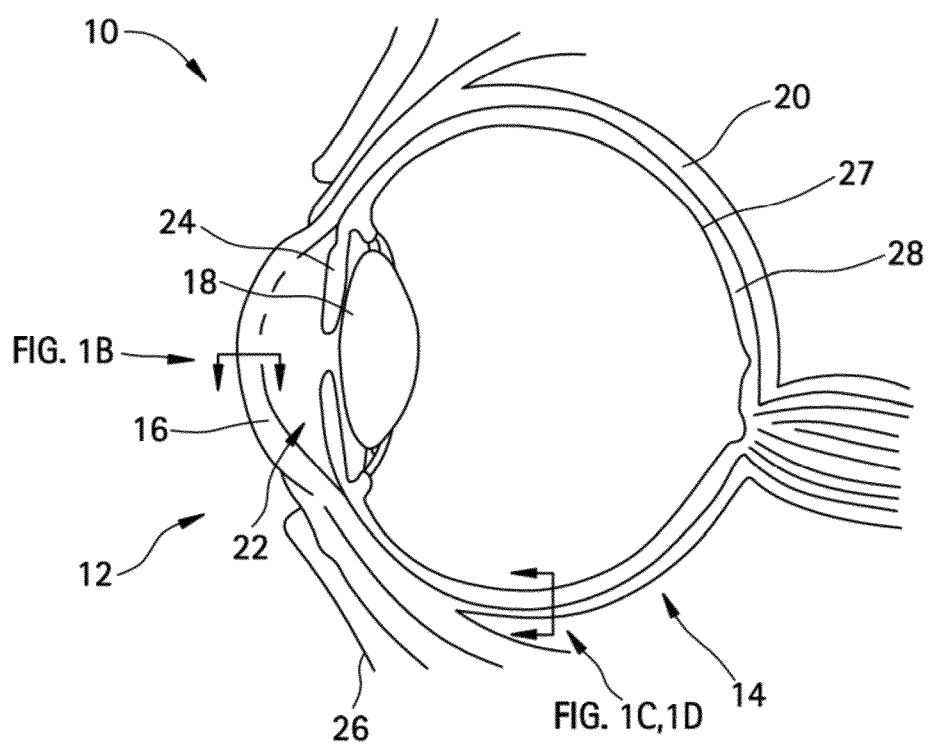
FIGS. 1A, 1B, 1C, and 1D are cross-sectional illustrations of the tissue structures of a human eye. The eye as a whole (1A), a close-up of the cornea (1B), and a close-up of the sclera and associated tissues in an eye without fluid in the suprachoroidal space (1C) or with fluid in the suprachoroidal space (1D).

An effective drug delivery system for delivery of a drug to the eye should optimally embody four general characteristics: first, it should be minimally invasive and safe; second, the drug should be administered in such a way that it is well targeted to the desired tissues and limits exposure to other regions of the eye; third, it should be capable of controlled or sustained delivery of the drug; and fourth, it should be as simple to use as possible. Embodiments of the present description address these needs by providing microneedle devices and methods of use to enhance the delivery of a drug to the eye.

In one advantageous and exemplary embodiment of the methods described herein, delivery of a drug is achieved by injecting (inserting) a microneedle into the sclera and injecting (infusing) a drug formulation through the inserted microneedle and into the suprachoroidal space of the eye. The microneedle is able to precisely deliver the drug into the suprachoroidal space for subsequent local delivery to nearby tissues in need of treatment. The drug may be released into the ocular tissues from the infused volume (or, e.g., from the microparticles therein) for an extended period, e.g., several hours or days or weeks or months, after the microneedle has been inserted and withdrawn. This beneficially can provide increased bioavailability of the drug relative, for example, to delivery by topical application of the drug formulation to ocular tissue surfaces. With the present microneedle, the method advantageously includes precise control of the depth of insertion into the ocular tissue, so that the microneedle tip can be placed into the suprachoroidal space or in the sclera but near enough to the suprachoroidal space for the infused drug formulation to flow into the suprachoroidal space. Advantageously, this may be accomplished without contacting underlying tissues, such as choroid and retina tissues.

Microneedles enable this delivery to be done in a minimally invasive manner superior to conventional needle approaches. For instance, the present microneedles advantageously may be inserted perpendicularly into the sclera, reaching the suprachoroidal space in a short penetration distance. This is in contrast to long conventional needles or cannula which must approach the suprachoroidal space at a steep angle, taking a longer penetration path through the sclera and other ocular tissue, increasing the size of the needle track and consequently increasing the risk of infection and/or vascular rupture. With such long needles, the ability to precisely control insertion depth is diminished relative to the microneedle approach described herein.

Advantageously, the delivery of the drug into the suprachoroidal space allows for the delivery of fluid drug formulation over a larger tissue area and to more difficult to target tissues in a single administration as compared to previously known needle devices. Not wishing to be bound by any theory, it is believed that upon entering the suprachoroidal space the fluid drug formulation flows circumferentially from the insertion site toward the retinochoroidal tissue, macula, and optic nerve in the posterior segment of the eye as well as anteriorly toward the uvea and ciliary body. In addition, a portion of the infused fluid drug formulation may remain in the sclera near the microneedle insertion site, serving as additional depot of the drug formulation that subsequently can diffuse into the suprachoroidal space and then into other adjacent tissues.

As used herein, the term "suprachoroidal space," which is synonymous with suprachoroid or suprachoroidia, describes the potential space in the region of the eye disposed between the sclera and choroid. This region primarily is composed of closely packed layers of long pigmented processes derived from each of the two adjacent tissues; however, a space can develop in this region as a result of fluid or other material buildup in the suprachoroidal space and the adjacent tissues. Those skilled in the art will appreciate that the suprachoroidal space frequently is expanded by fluid buildup because of some disease state in the eye or as a result of some trauma or surgical intervention. In the present description, however, the fluid buildup is intentionally created by infusion of a drug formulation into the suprachoroid to create the suprachoroidal space (which is filled with drug formulation). Not wishing to be bound by any theory, it is believed that this region serves as a pathway for uveoscleral outflow (i.e., a natural process of the eye moving fluid from one region of the eye to the other through) and becomes a real space in instances of choroidal detachment from the sclera.

Methods of Using the Microneedle

The microneedle devices described herein may be used to deliver drug formulations to the eye of a patient, particularly for the treatment, diagnosis, or prevention of ocular diseases. In a preferred embodiment, the patient is a human patient in need of treatment. The patient may be an adult or a child. In other embodiments, the patient may be a non-human mammal.

A wide range of ocular diseases and disorders may be treated by the methods and devices described herein. Non-limiting examples of ocular diseases include uveitis, glaucoma, diabetic macular edema or retinopathy, macular degeneration, and genetic diseases. The methods described herein are particularly useful for the local delivery of drugs that need to be administered to the posterior region of the eye, for example the retinochoroidal tissue, macula, and optic nerve in the posterior segment of the eye. In one embodiment, the delivery methods and devices described herein may be used in gene-based, therapy applications. For example, the methods may administer a fluid drug formulation into the suprachoroidal space to deliver select DNA, RNA, or oligonucleotides to targeted ocular tissues.

The microneedles can be used to target delivery to specific tissues or regions within the eye or in neighboring tissue. In various embodiments, the methods may be designed for drug delivery specifically to the sclera, the choroid, the Bruch's membrane, the retinal pigment epithelium, the subretinal space, the retina, the macula, the optic disk, the optic nerve, the ciliary body, the trabecular meshwork, the aqueous humor, the vitreous humor, and other ocular tissue or neighboring tissue in need of treatment.

Figure 1B:
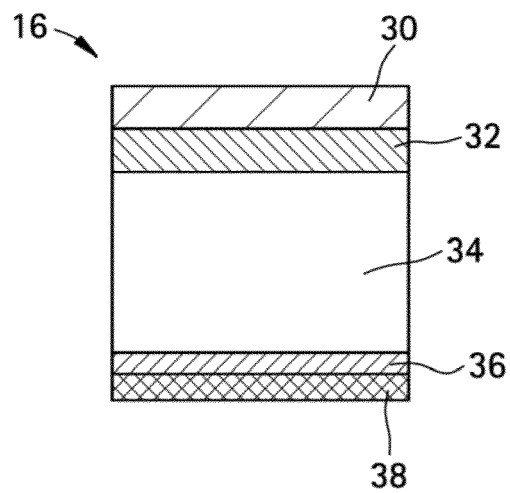
Figure 1C:
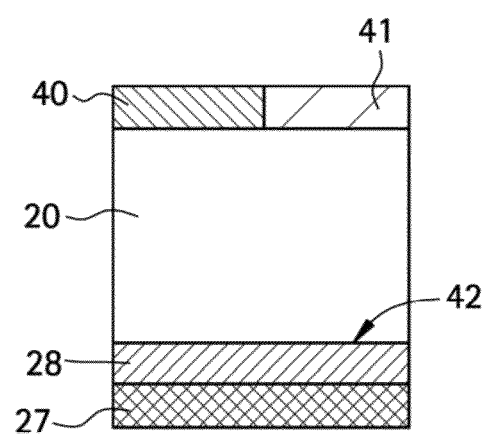
Figure 1D:
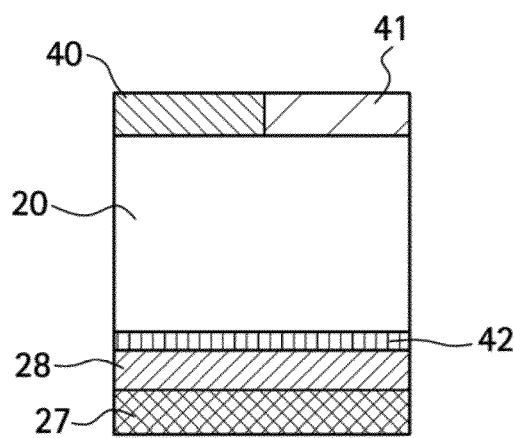
Figure 2:
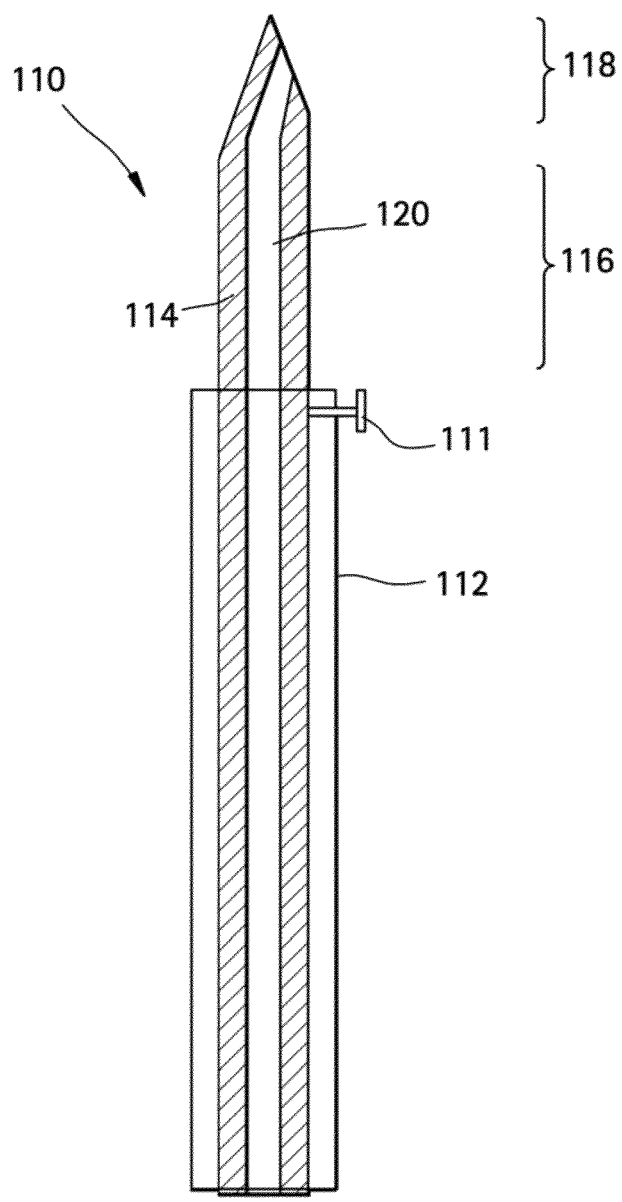
FIG. 2 is a cross-sectional view of a microneedle device comprising a hollow microneedle disposed in an elongated body according to one embodiment.

As used herein, "ocular tissue" and "eye" 10 include both the anterior segment 12 of the eye (i.e., the portion of the eye in front of the lens) and the posterior segment 14 of the eye (i.e., the portion of the eye behind the lens), as illustrated in FIG. 1A. The anterior segment 12 is bounded by the cornea 16 and the lens 18, while the posterior segment 14 is bounded by the sclera 20 and the lens 18. The anterior segment 12 is further subdivided into the anterior chamber 22, between the iris 24 and the cornea 16, and the posterior chamber 26, between the lens 18 and the iris 24. The exposed portion of the sclera 20 on the anterior segment 12 of the eye is protected by a clear membrane referred to as the conjunctiva (not shown). Underlying the sclera 20 is the choroid 28 and the retina 27, collectively referred to as retinochoroidal tissue. The loose connective tissue, or potential space, between the choroid 28 and the sclera 20 is referred to as the suprachoroidal space (not shown). FIG. 1B illustrates the cornea 16, which is composed of the epithelium 30, the Bowman's layer 32, the stroma 34, the Descemet's membrane 36, and the endothelium 38. FIG. 1C and FIG. 1D illustrate the sclera 20 with surrounding Tenon's Capsule 40 or conjunctiva 41, suprachoroidal space 42, choroid 28, and retina 27, both without and with a fluid in the suprachoroidal space, respectively.

The method of administering a drug to the eye generally comprises the steps of inserting a hollow microneedle into the sclera and then infusing a fluid drug formulation through the hollow microneedle and into the suprachoroidal space of the eye.

Insertion

In one embodiment, the insertion site is between the equator and the limbus of the eye. In another embodiment, the insertion site is between about 2 mm and about 10 mm posterior to the limbus of the eye. In embodiments, the insertion site of the microneedle is at about the equator of the eye. In another embodiment, the insertion site is between the equator and the limbus of the eye. In another embodiment, the insertion site is from 2 to 10 mm posterior to the limbus of the eye. In another embodiment, the drug formulation is introduced into the suprachoroidal space at the site of injection (i.e., at the tip of the microneedle) and then flows through the suprachoroidal space away from the site of injection while the injection occurs. In another embodiment, the site of injection (i.e., at the tip of the microneedle) is anterior to the equator of the eye and at least a portion of the drug formulation flows posterior to the equator of the eye during the injection (i.e., while drug formulation continues to flow out of the microneedle). In another embodiment, the site of injection (i.e., at the tip of the microneedle) is anterior to the equator of the eye and at least a portion of the drug formulation flows near the macular during the injection (i.e., while drug formulation continues to flow out of the microneedle).

Importantly, the depth of insertion of the microneedle into the ocular tissue is precisely controlled. Various methods can be used to control the insertion depth of the microneedles described herein. In a particular embodiment, the insertion depth is limited by the selected length or effective length of the microneedle. The "effective length" is that portion available for tissue insertion, i.e., the length that extends from the base and would be inserted if there were zero tissue deformation; it neglects any proximal portion of the microneedle that extends into or through the base and thus cannot be inserted in the tissue. That is, the microneedle may have a length approximately equal to the desired penetration depth. In one embodiment, the microneedle is short enough that tip of the microneedle may be inserted substantially to the base of the sclera (i.e., near the interface of the sclera and choroid) without completely penetrating across the sclera. In another embodiment, the tip of the microneedle is inserted through the sclera into the suprachoroidal space without penetrating through the choroid.

In another embodiment, the microneedles are designed to have a length longer than the desired penetration depth, but the microneedles are controllably inserted only part way into the tissue. Partial insertion may be controlled by the mechanical properties of the tissue, which bends and dimples during the microneedle insertion process. In this way, as a microneedle is inserted into the tissue, its movement partially elastically deforms the tissue and partially penetrates into the tissue. By controlling the degree to which the tissue deforms, the depth of microneedle insertion into the tissue can be controlled.

Additional insertion control features are described below in the "Control Features for Directing Movement of the Microneedle in the Methods of Use" section below.

In another embodiment, a microneedle is inserted into the tissue using a rotational/drilling technique and/or a vibrating action. In this way, the microneedle can be inserted to a desired depth by, for example, drilling the microneedles a desired number of rotations, which corresponds to a desired depth into the tissue. See, e.g., U.S. Patent Application Publication No. 20050137525 A1 to Wang et al., which is incorporated herein by reference, for a description of drilling microneedles. The rotational/drilling technique and/or a vibrating action may be applied during the insertion step, retraction step, or both.

Infusion

In a preferred embodiment, the fluid drug formulation is infused into the suprachoroidal space through a hollow microneedle by driving the drug formulation from a source reservoir into the ocular tissue using a pressure gradient (e.g., pumping, syringe). In other embodiments, the drug formulation may be driven from a source reservoir into the ocular tissue using an electric field (e.g., iontophoresis) or another externally applied energy (e.g., ultrasound/acoustic energy).

In one embodiment, the amount of fluid drug formulation infused into the suprachoroidal space from the inserted microneedle is from 10 microliter to 200 microliter, e.g., from 50 to 150 µL. In another embodiment, from about 10 microliter to about 500 microliter, e.g., from 50 to 250 µL, is infused through the microneedle into the suprachoroidal space.

In one embodiment, the driving force or pressure infusing the fluid drug formulation through the microneedle causes the infused drug formulation to flow within the suprachoroidal space and reach the back of the eye during the administration (i.e., during the infusion) process. This may occur in less than one or two minutes, such as 1 sec to 100 sec, e.g., 10 to 30 seconds. In one aspect, the fluid drug formulation desirably flows circumferentially within the suprachoroidal space during the infusion process to a site that is at least 2.5 mm away from the insertion site, to a site that is at least 5 mm away from the insertion site, or to a site that is at least 10 mm away from the insertion site. Desirably, the fluid drug formulation flows circumferentially within the suprachoroidal space from the insertion site toward the back of the eye (i.e., the retinochoroidal tissue, macula, and optic nerve in the posterior segment of the eye).

The amount of drug delivered within the ocular tissue also may be controlled, in part, by the type of microneedle used and how it is used. In one exemplary embodiment, a hollow microneedle is inserted into the ocular tissue and progressively retracted from the ocular tissue after insertion to deliver a fluid drug, where after achieving a certain dosage, the delivery could be stopped by deactivating the fluid driving force, such as pressure (e.g., from a mechanical device such as a syringe) or an electric field, to avoid leakage/uncontrolled deliver of drug. Desirably, the amount of drug being delivered is controlled by driving the fluid drug formulation at a suitable infusion pressure. In certain embodiments, the infusion pressure may be at least 150 kPa, at least 250 kPa, or at least 300 kPa. Suitable infusion pressures may vary with the particular patient or species.

Those skilled in the art will appreciate, however, that the desired infusion pressure to deliver a suitable amount of fluid drug formulation may be influenced by the depth of insertion of the microneedle and the composition of the fluid drug formulation. For example, a greater infusion pressure may be required in embodiments wherein the drug formulation for delivery into the eye is in the form of or includes nanoparticles or microparticles encapsulating the active agent or microbubbles. Nanoparticle or microparticle encapsulation techniques are well known in the art.

Additional infusion control features are described below in the "Control of Transport Through Microneedle" section below.

Figure 6A:
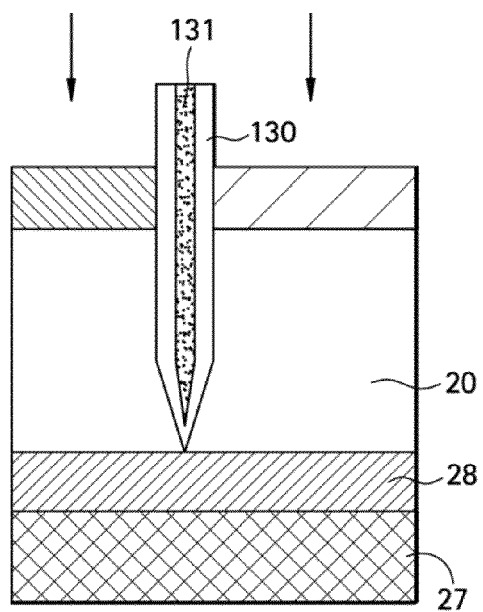
FIGS. 6A and 6B illustrate an embodiment of a process for using a hollow microneedle to deliver drug into the suprachoroidal space of an eye, where the process includes inserting the hollow microneedle into the sclera and infusion of a fluid drug formulation into the suprachoroidal space.
Figure 6B:
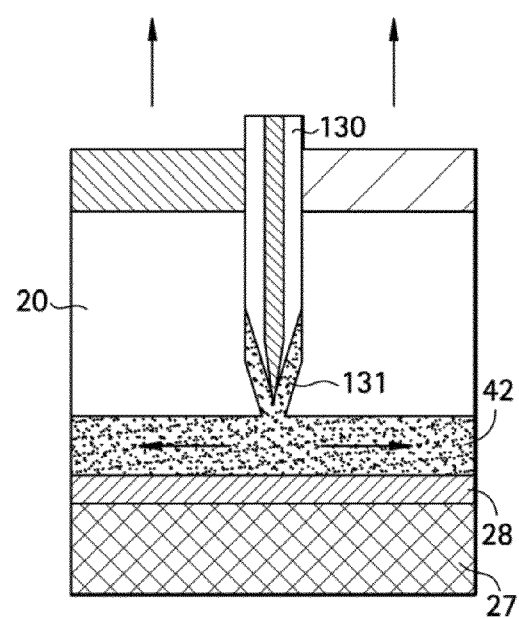

In one embodiment, the method of administering a drug to the eye may further include partially retracting the hollow microneedle after the insertion step and before and/or during the infusion of the drug formulation. In a particular embodiment, the partial retraction of the microneedle occurs prior to the step of infusing the fluid drug formulation into the ocular tissue. This insertion/retraction step may form a pocket and beneficially permits the fluid drug formulation to flow out of the microneedle unimpeded or less impeded by ocular tissue at the opening at the tip portion of the microneedle. This pocket may be filled with drug formulation, but also serves as a conduit through with fluid drug formulation can flow from the microneedle, through the pocket and into the suprachoroidal space. FIG. 6A shows a hollow microneedle 130 inserted into the sclera 20, with drug formulation 131 temporarily positioned in the hollow bore of the microneedle. (The fluid communication to a reservoir of the fluid drug formulation is not shown.) FIG. 6B shows the microneedle 130 following partial retraction and infusion of the fluid drug formulation 131 into the suprachoroidal space. Arrows show the circumferential flow of the drug formulation through the suprachoroidal space.

In a particular embodiment, the microneedle infuses a drug formulation through the sclera into the suprachoroidal space for controlled (i.e., sustained, extended, or modulated over time) release of a drug to one or more ocular or neighboring tissues. This "sustained release" or "extended release" or "modulated release" is generally more prolonged than that obtainable by topical application of the drug formulation to the ocular tissue. In a particular embodiment, there is an extended, sustained or modulated release of the drug formulation after at least one microneedle is withdrawn from the ocular tissue. This delivery method can be particularly advantageous with ocular tissues, where it is desirable for the insertion and withdrawal process to occur over as short a period as possible to minimize patient discomfort—in contrast to transdermal microneedle patch applications, where patches may more likely be worn (with microneedles inserted) over an extended period without patient discomfort.

Other Steps, Embodiments, and Applications

Figure 18:
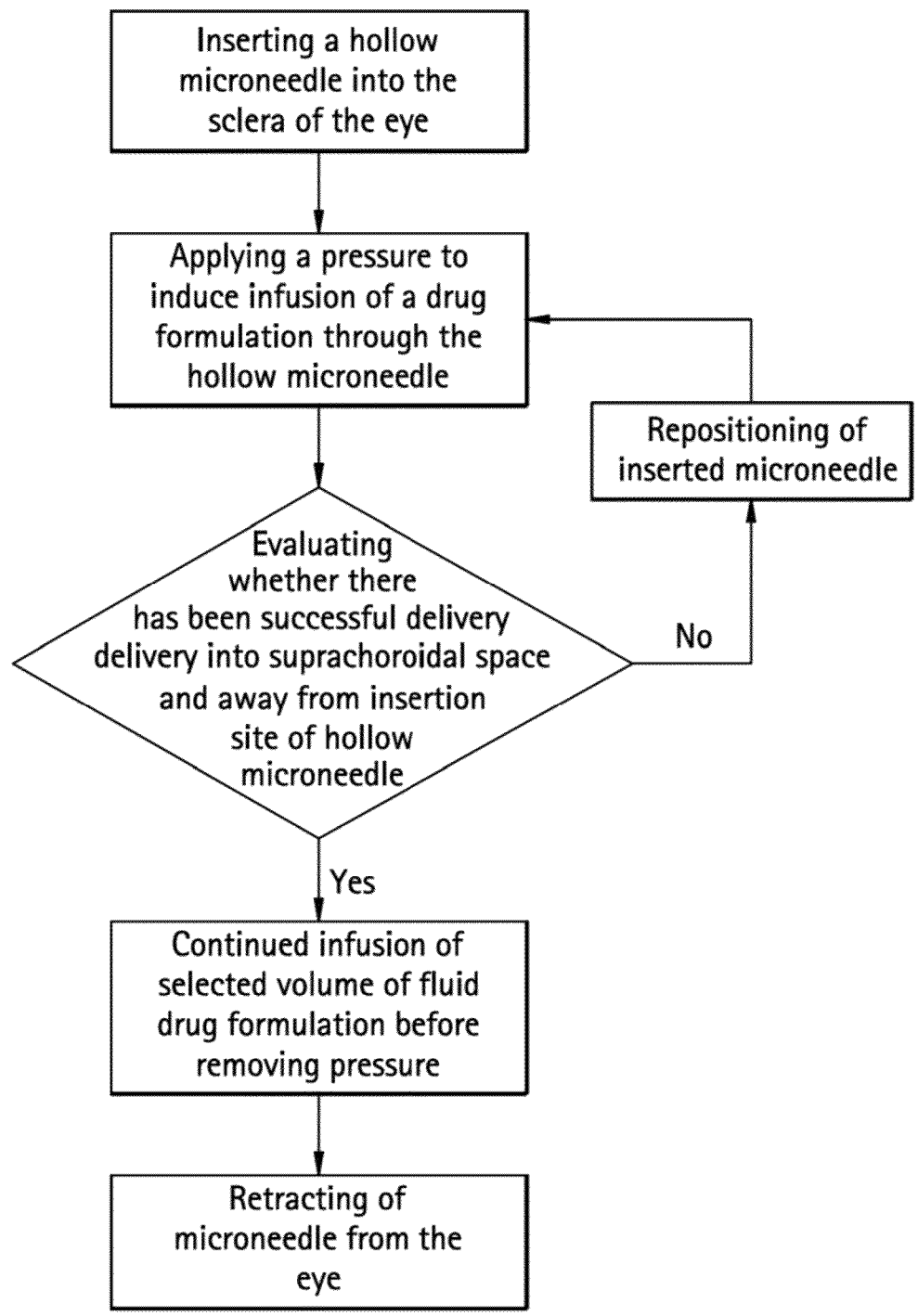
FIG. 18 is a block diagram of a method for administering a drug to the eye according to one embodiment.

In another aspect, the method of administering a drug to an eye of a patient may include monitoring the insertion of the microneedle and/or infusion of the fluid drug formulation to ensure precise delivery of the fluid drug formulation to the suprachoroidal space (FIG. 18). Such monitoring may be achieved using imaged-guided feedback methods during one or more of these steps, non-limiting examples of which include conventional microscopy, MRI, x-ray, confocal microscopy, ocular coherence tomography (e.g., anterior segment optical coherence tomography, Heidelberg retina tomography, spectral domain optical coherence tomography), fluorescein angiography, indocyanine green angiography, high resolution stereoscopic fundus photography, autofluorescence imaging, ultra-wide field imaging, and various ultrasound techniques. Thus, the method may further comprise determining whether an initial infusion of the fluid drug formulation has flowed into the suprachoroidal space of the eye and away from the insertion site. If it is determined that an initial infusion has been successful, a desired volume of the fluid drug formulation can be infused and the infusion discontinued by removing the fluid driving force, such as pressure, and retracting the microneedle from the eye. If, however, it is determined that the initial infusion of the fluid drug formulation has been unsuccessful (i.e., substantially none of the drug formulation has flowed into the suprachoroidal space of the eye and away from the insertion site), then the microneedle may be repositioned and the process repeated until a successful delivery is achieved.

The microneedle optionally may be part of an array of two or more microneedles such that the method further includes inserting at least a second microneedle into the sclera without penetrating across the sclera. In one embodiment wherein an array of two or more microneedles are inserted into the ocular tissue, the drug formulation of each of the two or more microneedles may be identical to or different from one another, in drug, formulation, volume/quantity of drug formulation, or a combination of these parameters. In one case, different types of drug formulations may be injected via the one or more microneedles. For example, inserting a second hollow microneedle comprising a second drug formulation into the ocular tissue will result in delivery of the second drug formulation into the ocular tissue.

The microneedle devices described herein may be adapted to remove substances, such as a fluid, tissue, or molecule sample, from the eye.

Those skilled in the art will appreciate, however, that other types of microneedles (e.g., solid microneedles) and other methods of delivering the drug formulation into the ocular tissue may be used instead of or in conjunction with the infusion methods described herein. Non-limiting examples include dissolving, at least in part, a coating of a drug formulation off of a microneedle; detaching, at least in part, a coating of a drug formulation (e.g., as a substantially intact sleeve or in fragments) off of a microneedle; breaking or dissolving a microneedle off of a base to which the microneedle is integrally formed or is connected; or any combination thereof.

The microneedle devices described herein also may be adapted to use the one or more microneedles as a sensor to detect analytes, electrical activity, and optical or other signals. The sensor may include sensors of pressure, temperature, chemicals, and/or electromagnetic fields (e.g., light). Biosensors can be located on or within the microneedle, or inside a device in communication with the body tissue via the microneedle. The microneedle biosensor can be any of the four classes of principal transducers: potentiometric, amperometric, optical, and physiochemical. In one embodiment, a hollow microneedle is filled with a substance, such as a gel, that has a sensing functionality associated with it. In an application for sensing based on binding to a substrate or reaction mediated by an enzyme, the substrate or enzyme can be immobilized in the needle interior. In another embodiment, a wave guide can be incorporated into the microneedle device to direct light to a specific location, or for detection, for example, using means such as a pH dye for color evaluation. Similarly, heat, electricity, light, ultrasound or other energy forms may be precisely transmitted to directly stimulate, damage, or heal a specific tissue or for diagnostic purposes.

The Microneedle Device

The microneedle device includes a hollow microneedle. The device may include an elongated housing for holding the proximal end of the microneedle. The device may further include a means for conducting a fluid drug formulation through the microneedle. For example, the means may be a flexible or rigid conduit in fluid connection with the base or proximal end of the microneedle. The means may also include a pump or other devices for creating a pressure gradient for inducing fluid flow through the device. The conduit may in operable connection with a source of the fluid drug formulation. The source may be any suitable container. In one embodiment, the source may be in the form of a conventional syringe. The source may be a disposable unit dose container.

Microneedle

As used herein, the term "hollow" includes a single, straight bore through the center of the microneedle, as well as multiple bores, bores that follow complex paths through the microneedles, multiple entry and exit points from the bore(s), and intersecting or networks of bores. That is, a hollow microneedle has a structure that includes one or more continuous pathways from the base of the microneedle to an exit point in the shaft and/or tip portion of the microneedle distal to the base.

As used herein, the term "microneedle" refers to a conduit body having a base, a shaft, and a tip end suitable for insertion into the sclera and other ocular tissue and has dimensions suitable for minimally invasive insertion and fluid drug formulation infusion as described herein. That is, the microneedle has a length or effective length that does not exceed 2000 microns and a width (or diameter) that does not exceed 500 microns.

In various embodiments, the microneedle may have a length of about 50 µm to 2000 µm. In another particular embodiment, the microneedle may have a length of about 150 µm to about 1500 µm, about 300 µm to about 1250 µm, about 500 µm to about 1250 µm, about 700 µm to about 1000 µm, or about 800 to about 1000 µm. In a preferred embodiment, the length of the microneedle is about 1000 µm. In various embodiments, the proximal portion of the microneedle has a maximum width or cross-sectional dimension of about 50 µm to 500 µm, about 50 µm to about 400 µm, about 100 µm to about 400 µm, about 200 µm to about 400 µm, or about 100 µm to about 250 µm, with an aperture diameter of about 5 µm to about 400 µm. In a particular embodiment, the proximal portion of the microneedle has a maximum width or cross-sectional dimension of about 400 µm. Those skilled in the art will appreciate, however, that in embodiments in which the tip of the microneedle is beveled that the aperture diameter may be greater than the outer diameter of the proximal portion of the microneedle. The microneedle may be fabricated to have an aspect ratio (width:length) of about 1:1.5 to about 1:10. Other lengths, widths, and aspect ratios are envisioned.

The microneedle can have a straight or tapered shaft. In one embodiment, the diameter of the microneedle is greatest at the base end of the microneedle and tapers to a point at the end distal the base. The microneedle can also be fabricated to have a shaft that includes both a straight (i.e., untapered) portion and a tapered (e.g., beveled) portion. The microneedles can be formed with shafts that have a circular cross-section in the perpendicular, or the cross-section can be non-circular. The tip portion of the microneedles can have a variety of configurations. The tip of the microneedle can be symmetrical or asymmetrical about the longitudinal axis of the shaft. The tips may be beveled, tapered, squared-off, or rounded. In particular embodiments, the microneedle may be designed such that the tip portion of the microneedle is substantially the only portion of the microneedle inserted into the ocular tissue (i.e., the tip portion is greater than 75% of the total length of the microneedle, greater than 85% of the total length of the microneedle, or greater than about 95% of the total length of the microneedle). In other particular embodiments, the microneedle may be designed such that the tip portion is only a portion of the microneedle that is inserted into the ocular tissue and generally has a length that is less than about 75% of the total length of the microneedle, less than about 50% of the total length of the microneedle, or less than about 25% of the total length of the microneedle. For example, in one embodiment the microneedle has a total effective length between 500 µm and 1000 µm, wherein the tip portion has a length that is less than about 400 µm, less than about 300 µm, or less than about 200 µm.

Base

The microneedle extends from a base. The base may be integral with or separate from the microneedle. The base may be rigid or flexible. The base may be substantially planar or it may be curved, for example, in the shape of the ocular tissue surface at the site of injection or, for example, curved away from the ocular surface (e.g., convex) so as to minimize contact between the base and the ocular tissue. Desirably, the base is shaped to provide minimal contact with the surface of the eye at the point of insertion. For example, in one embodiment, the base may extend only a minimal distance from the microneedle shaft substantially perpendicular. In another embodiment, the base may be shaped so as to elevate the ocular tissue towards the microneedle so as to counteract the deflection of the ocular tissue and facilitate insertion of the microneedle into the ocular tissue (e.g., the base may extend from the microneedle toward the tip portion of the microneedle so as to "pinch" the ocular tissue). Some such embodiments may be based, at least in part, on the devices described in U.S. Pat. No. 6,743,211, the relevant disclosure of which is incorporated herein by reference.

Figure 5:
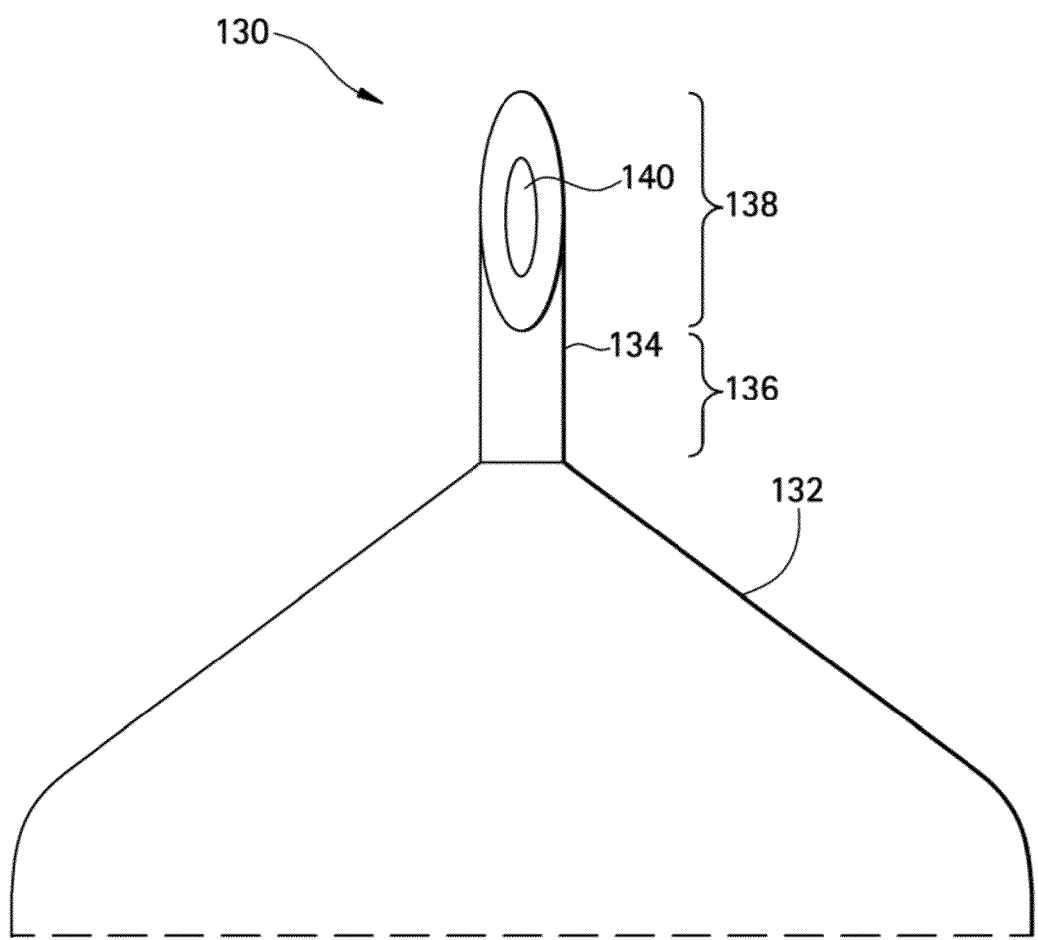
FIG. 5 is an illustration of a microneedle device according to one embodiment.

In a particular embodiment, the microneedle device has a single microneedle. In one embodiment, illustrated in FIG. 5, the microneedle device 130 includes a convex base 132 and a hollow microneedle 134 which has a bore 140 through which a fluid drug formulation (not shown) can be delivered to the eye or through which a biological fluid can be withdrawn from the eye. The hollow microneedle 134 includes a proximal portion 136 and a tip portion 138.

The microneedle may extend from the base of the microneedle device at any angle suitable for insertion into the eye. In a particular embodiment, the microneedle extends from the base at an angle of about 90 degrees to provide approximately perpendicular insertion of the microneedles into the surface of the eye. In another particular embodiment, the microneedle extends from the base at an angle from about 60 to about 90 degrees.

Microneedle Arrays

In an alternative embodiment, the device includes an array of two or more microneedles. For example, the device may include an array of between 2 and 1000 (e.g., between 2 and 100) microneedles. In one embodiment, a device may include between 1 and 10 microneedles. An array of microneedles may include a mixture of different microneedles. For instance, an array may include microneedles having various lengths, base portion diameters, tip portion shapes, spacings between microneedles, drug coatings, etc. In embodiments wherein the microneedle device comprises an array of two or more microneedles, the angle at which a single microneedle extends from the base may be independent from the angle at which another microneedle in the array extends from the base.

Exemplary Devices

Figure 3:
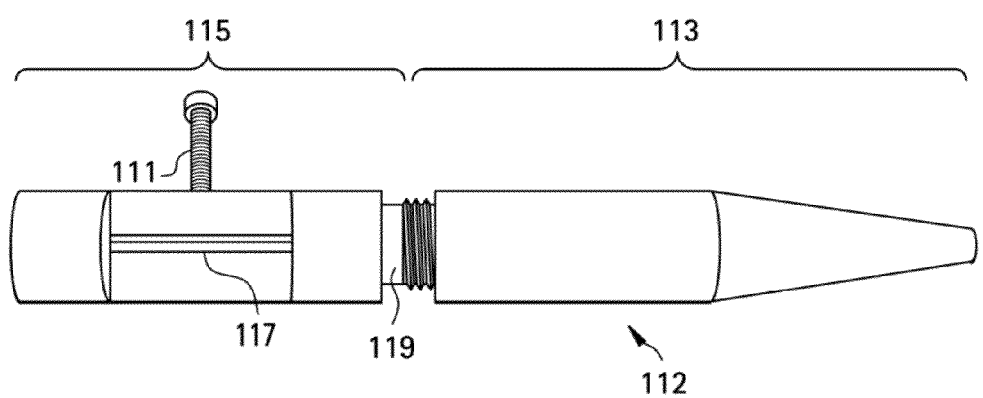
FIG. 3 is a cross-sectional view of the elongated body of the microneedle devices shown in FIG. 2.
Figure 4:
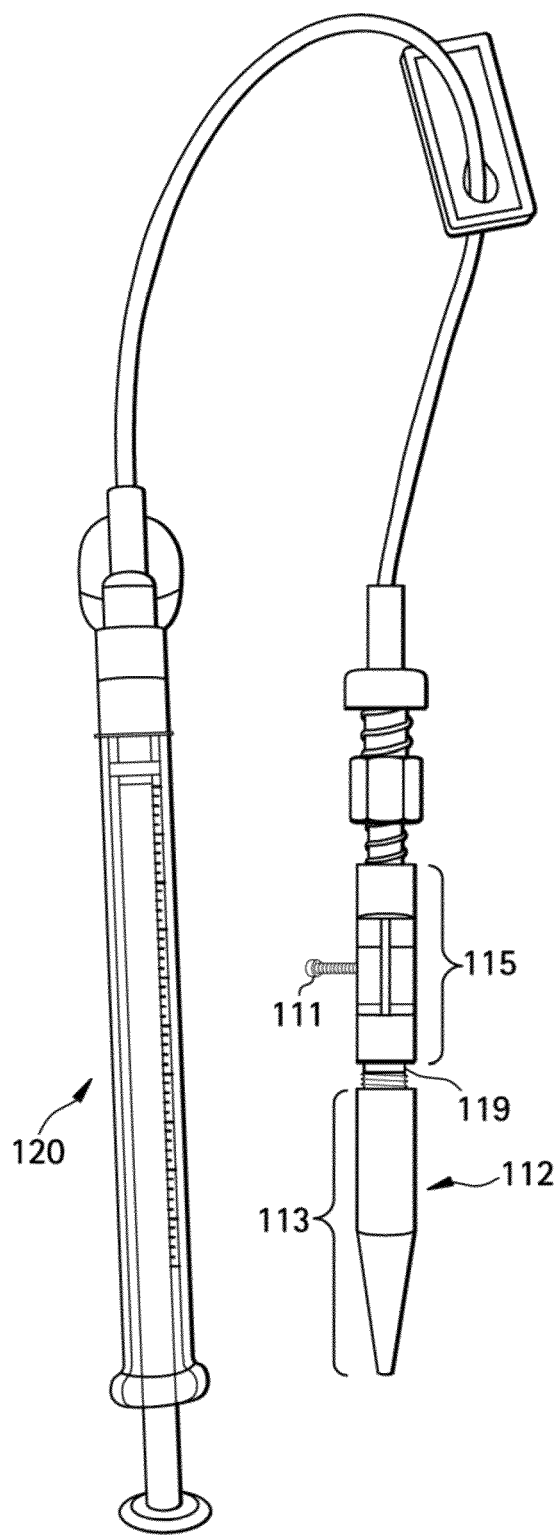
FIG. 4 is an illustration of a microneedle device according to one embodiment.

FIGS. 2-5 illustrate exemplary embodiments of microneedle devices. In one embodiment, illustrated in FIG. 2-3, the microneedle device 110 includes a hollow microneedle 114 having a hollow bore 140 through which a fluid drug formulation (not shown) can be delivered to the eye or through which a biological fluid can be withdrawn from the eye. The microneedle includes a proximal portion 116 and a tip portion 118. The microneedle 114 may extend from a base comprising, for example, an elongated body 112 having a distal end from which the proximal portion 116 and tip portion 118 of the microneedle extends. The elongated body may further comprise a means for securing 111 a base portion of the microneedle extending beyond the distal end of the base 112, such as a screw or pin. An exemplary embodiment of the elongated body 112 for securing the microneedle is illustrated in FIG. 3, and comprises a cap portion 113 and a base portion 115 having a hollow bore 117 therein. The cap portion 113 and base portion 115 of the elongated body 112 desirably comprise a means for manually adjusting the length of needle (i.e., the proximal portion and tip portion of the microneedle extending from the base 112) protruding out of the cap portion of the elongated body. Such means may include, for example, threads 119 allowing the cap portion 113 to be screwed in and out of the base portion 115 of the elongated body. In an exemplary embodiment illustrated in FIG. 4, the base portion 115 of the elongated body may be operably connected to an actuator 120 for controlled infusion of the fluid drug formulation through the microneedle into the suprachoroidal space.

The microneedle device may further comprise a fluid reservoir for containing the fluid drug formulation, the fluid drug reservoir being in operable communication with the bore of the microneedle at a location distal to the tip end of the microneedle. The fluid reservoir may be integral with the microneedle, integral with the elongated body, or separate from both the microneedle and elongated body.

Fabrication of the Microneedles

The microneedle can be formed/constructed of different biocompatible materials, including metals, glasses, semiconductor materials, ceramics, or polymers. Examples of suitable metals include pharmaceutical grade stainless steel, gold, titanium, nickel, iron, gold, tin, chromium, copper, and alloys thereof. The polymer can be biodegradable or non-biodegradable. Examples of suitable biocompatible, biodegradable polymers include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes and copolymers and blends thereof. Representative non-biodegradable polymers include various thermoplastics or other polymeric structural materials known in the fabrication of medical devices. Examples include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof. Biodegradable microneedles can provide an increased level of safety compared to non-biodegradable ones, such that they are essentially harmless even if inadvertently broken off into the ocular tissue.

The microneedle can be fabricated by a variety of methods known in the art or as described in the Examples below. In one embodiment, the hollow microneedle is fabricated using a laser or similar optical energy source. In one example, a microcannula may be cut using a laser to represent the desired microneedle length. The laser may also be use to shape single or multiple tip openings. Single or multiple cuts may be performed on a single microcannula to shape the desired microneedle structure. In one example, the microcannula may be made of metal such as stainless steel and cut using a laser with a wavelength in the infrared region of the light spectrum (0.7-300 µm). Further refinement may be performed using metal electropolishing techniques familiar to those in the field. In another embodiment, the microneedle length and optional bevel is formed by a physical grinding process, which for example may include grinding a metal cannula against a moving abrasive surface. The fabrication process may further include precision grinding, micro-bead jet blasting and ultrasonic cleaning to form the shape of the desired precise tip of the microneedle.

Further details of possible manufacturing techniques are described, for example, in U.S. Patent Application Publication No. 2006/0086689 A1 to Raju et al., U.S. Patent Application Publication No. 2006/0084942 to Kim et al., U.S. Patent Application Publication No. 2005/0209565 to Yuzhakov et al., U.S. Patent Application Publication No. 2002/0082543 A1 to Park et al., U.S. Pat. No. 6,334,856 to Allen et al., U.S. Pat. No. 6,611,707 to Prausnitz et al., U.S. Pat. No. 6,743,211 to Prausnitz et al., all of which are incorporated herein by reference for their disclosure of microneedle fabrication techniques.

Fluid Drug Formulation

The fluid drug formulation may be in the form of a liquid drug, a liquid solution that includes a drug in a suitable solvent, or liquid suspension. The liquid suspension may include microparticles or nanoparticles dispersed in a suitable liquid vehicle for infusion. In various embodiments, the drug may be included in the liquid vehicle, in the microparticles or nanoparticles, or in both the vehicle and particles. The fluid drug formulation is sufficiently fluid to flow into and within the suprachoroidal space. In a preferred embodiment, the viscosity of the fluid drug formulation is about 1 cP at 37° C.

A wide range of drugs may be formulated for delivery to ocular tissues with the present microneedle devices and methods. As used herein, the term "drug" refers to essentially any prophylactic, therapeutic, or diagnostic agent, i.e., an ingredient useful for medical, veterinary, or cosmetic applications. The drug may be selected from suitable proteins, peptides and fragments thereof, which can be naturally occurring, synthesized or recombinantly produced. The drug may be selected from suitable oligonucleotides (e.g., antisense oligonucleotide agents), polynucleotides (e.g., therapeutic DNA), ribozymes, dsRNAs, siRNA, RNAi, gene therapy vectors, and/or vaccines for therapeutic use. The drug may be an aptamer (e.g., an oligonucleotide or peptide molecule that binds to a specific target molecule).

Representative examples of types of drugs for delivery to ocular tissues include antibiotics, antiviral agents, analgesics, anesthetics, antihistamines, anti-inflammatory agents, and antineoplastic agents. Non-limiting examples of specific drugs and classes of drugs include β-adrenoceptor antagonists (e.g., carteolol, cetamolol, betaxolol, levobunolol, metipranolol, timolol), miotics (e.g., pilocarpine, carbachol, physostigmine), sympathomimetics (e.g., adrenaline, dipivefrine), carbonic anhydrase inhibitors (e.g., acetazolamide, dorzolamide), prostaglandins, anti-microbial compounds, including anti-bacterials and anti-fungals (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines), anti-viral compounds (e.g., acyclovir, cidofovir, idoxuridine, interferons), aldose reductase inhibitors, anti-inflammatory and/or anti-allergy compounds (e.g., steroidal compounds such as betamethasone, clobetasone, dexamethasone, fluorometholone, hydrocortisone, prednisolone and non-steroidal compounds such as antazoline, bromfenac, diclofenac, indomethacin, lodoxamide, saprofen, sodium cromoglycate), artificial tear/dry eye therapies, local anesthetics (e.g., amethocaine, lignocaine, oxybuprocaine, proxymetacaine), cyclosporine, diclofenac, urogastrone and growth factors such as epidermal growth factor, mydriatics and cycloplegics, mitomycin C, and collagenase inhibitors and treatments of age-related macular degeneration such as pegagtanib sodium, ranibizumab, and bevacizumab. In certain embodiments the drug may be an integrin antagonist, a selectin antagonist, an adhesion molecule antagonist (e.g., Intercellular Adhesion Molecule (ICAM)-1, ICAM-2, ICAM-3, Platelet Endothelial Adhesion Molecule (PCAM), Vascular Cell Adhesion Molecule (VCAM)), or a leukocyte adhesion-inducing cytokine or growth factor antagonist (e.g., Tumor Neucrosis Factor-α (TNF-α), Interleukin-1β (IL-1β), Monocyte Chemotatic Protein-1 (MCP-1) and a Vascular Endothelial Growth Factor (VEGF)), as described in U.S. Pat. No. 6,524,581 to Adamis. In certain other embodiments, the drug may be sub-immunoglobulin antigen-binding molecules, such as Fv immunoglobulin fragments, minibodies, and the like, as described in U.S. Pat. No. 6,773,916 to Thiel et al. In another embodiment, the drug may be a diagnostic agent, such as a contrast agent, known in the art.

The drug typically needs to be formulated for storage and delivery via the microneedle device described herein. The "drug formulation" is a formulation of a drug, which typically includes one or more pharmaceutically acceptable excipient materials known in the art. The term "excipient" refers to any non-active ingredient of the formulation intended to facilitate handling, stability, dispersibility, wettability, release kinetics, and/or injection of the drug. In one embodiment, the excipient may include or consist of water or saline.

In one embodiment, the fluid drug formulation includes microparticles or nanoparticles, either of which includes at least one drug. Desirably, the microparticles or nanoparticles provide for the controlled release of drug into the ocular tissue. As used herein, the term "microparticle" encompasses microspheres, microcapsules, microparticles, and beads, having a number average diameter of 1 to 100 μm, most preferably 1 to 25 μm. The term "nanoparticles" are particles having a number average diameter of 1 to 1000 nm. Microparticles may or may not be spherical in shape. "Microcapsules" are defined as microparticles having an outer shell surrounding a core of another material. The core can be liquid, gel, solid, gas, or a combination thereof. In one case, the microcapsule may be a "microbubble" having an outer shell surrounding a core of gas, wherein the drug is disposed on the surface of the outer shell, in the outer shell itself, or in the core. (Microbubbles may be respond to acoustic vibrations as known in the art for diagnosis or to burst the microbubble to release its payload at/into a select ocular tissue site.) "Microspheres" can be solid spheres, can be porous and include a sponge-like or honeycomb structure formed by pores or voids in a matrix material or shell, or can include multiple discrete voids in a matrix material or shell. The microparticle or nanoparticles may further include a matrix material. The shell or matrix material may be a polymer, amino acid, saccharide, or other material known in the art of microencapsulation.

The drug-containing microparticles or nanoparticles may be suspended in an aqueous or non-aqueous liquid vehicle. The liquid vehicle may be a pharmaceutically acceptable aqueous solution, and optionally may further include a surfactant. The microparticles or nanoparticles of drug themselves may include an excipient material, such as a polymer, a polysaccharide, a surfactant, etc., which are known in the art to control the kinetics of drug release from particles.

In one embodiment, the fluid drug formulation further includes an agent effective to degrade collagen or GAG fibers in the sclera, which may enhance penetration/release of the drug into the ocular tissues. This agent may be, for example, an enzyme, such a hyaluronidase, a collagenase, or a combination thereof. In a variation of this method, the enzyme is administered to the ocular tissue in a separate step from—preceding or following—infusion of the drug. The enzyme and drug are administered at the same site.

In another embodiment, the drug formulation is one which undergoes a phase change upon administration. For instance, a liquid drug formulation may be injected through hollow microneedles into the suprachoroidal space, where it then gels and the drug diffuses out from the gel for controlled release.

Control Features for Directing Movement of the Microneedle in the Methods of Use The microneedle device may comprise a means for controllably inserting, and optionally retracting, the microneedle into the ocular tissue. In addition, the microneedle device may include means of controlling the angle at which the at least one microneedle is inserted into the ocular tissue (e.g., by inserting the at least one microneedle into the surface of the ocular tissue at an angle of about 90 degrees).

The depth of microneedle insertion into the ocular tissue can be controlled by the length of the microneedle, as well as other geometric features of the microneedle. For example, a flange or other a sudden change in microneedle width can be used to limit the depth of microneedle insertion. The microneedle insertion can also be controlled using a mechanical micropositioning system involving gears or other mechanical components that move the microneedle into the ocular tissue a controlled distance and, likewise, can be operated, for example, in reverse, to retract the microneedle a controlled distance. The depth of insertion can also be controlled by the velocity at which the microneedle is inserted into the ocular tissue. The retraction distance can be controlled by elastic recoil of the ocular tissue into which the microneedle is inserted or by including an elastic element within the microneedle device that pulls the microneedle back a specified distance after the force of insertion is released.

The angle of insertion can be directed by positioning the microneedle at a first angle relative to the microneedle base and positioning the base at a second angle relative to the ocular surface. In one embodiment, the first angle can be about 90° and the second angle can be about 0°. The angle of insertion can also be directed by having the microneedle protrude from a device housing through a channel in that housing that is oriented at a specified angle.

One skilled in the art may adapt mechanical systems known in the art in combination with the disclosure set forth herein and in the Examples below to devise suitable structures to controllably drive the microneedle insertion, which structures may be manually operable, electromechanically operable, or a combination thereof.

Control of Transport Through Microneedle

The transport of drug formulation or biological fluid through a hollow microneedle can be controlled or monitored using, for example, one or more valves, pumps, sensors, actuators, and microprocessors. For instance, in one embodiment the microneedle device may include a micropump, microvalve, and positioner, with a microprocessor programmed to control a pump or valve to control the rate of delivery of a drug formulation through the microneedle and into the ocular tissue. The flow through a microneedle may be driven by diffusion, capillary action, a mechanical pump, electroosmosis, electrophoresis, convection or other driving forces. Devices and microneedle designs can be tailored using known pumps and other devices to utilize these drivers. In one embodiment, the microneedle device may further include an iontophoretic apparatus, similar to that described in U.S. Pat. No. 6,319,240 to Beck, for enhancing the delivery of the drug formulation to the ocular tissue. In another embodiment the microneedle devices can further include a flowmeter or other means to monitor flow through the microneedles and to coordinate use of the pumps and valves.

The flow of drug formulation or biological fluid can be regulated using various valves or gates known in the art. The valve may be one which can be selectively and repeatedly opened and closed, or it may be a single-use type, such as a fracturable barrier. Other valves or gates used in the microneedle devices can be activated thermally, electrochemically, mechanically, or magnetically to selectively initiate, modulate, or stop the flow of material through the microneedles. In one embodiment, the flow is controlled with a rate-limiting membrane acting as the valve.

The present invention may be further understood with reference to the following non-limiting examples.

EXAMPLES

Experiments were conducted to evaluate whether microneedles could be used to pierce to the base of the sclera and target the suprachoroidal space. More specifically, experiments were conducted to evaluate whether hollow microneedles can deliver small molecules and particles to the suprachoroidal space of pig, rabbit and human cadaver eyes. Additional experiments were conducted to measure the effect of microneedle length, infusion pressure, and intraocular pressure on the delivery of particles ranging from 20-1000 nm in diameter in pig eyes. Finally, experiments were conducted to examine the role that particle size plays and the influence of ocular anatomical barriers on delivery to the suprachoroidal space.

Whole rabbit eyes (Pel-Freez Biologicals, Rogers, Ark.), pig eyes (Sioux-Preme Packing, Sioux Center, Iowa) and human eyes (Georgia Eye Bank, Atlanta, Ga.), all with the optic nerve attached, were shipped on ice and stored wet at 4° C. for up to 3 days. Prior to use, eyes were allowed to come to room temperature and any fat and conjunctiva were removed to expose the sclera.

Figure 7A:
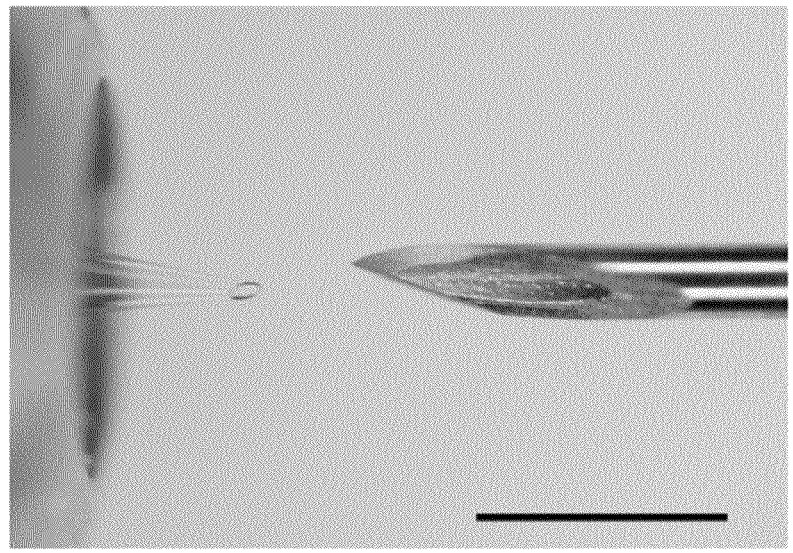
FIG. 7A shows a comparison of a hollow microneedle according to one embodiment as compared to the tip of a conventional 30 gauge hypodermic needle.

Hollow microneedles were fabricated from borosilicate micropipette tubes (Sutter Instrument, Novato, Calif.), as described previously (J. Jiang, et al., *Pharm. Res.* 26:395-403 (2009)). FIG. 7A shows a comparison of the hollow microneedle compared to the tip of a 30 gauge hypodermic needle (scale=500 µm). A custom, pen-like device with a threaded cap was fabricated to position the microneedle and allow precise adjustment of its length. This device was attached to a micropipette holder (MMP-KIT, World Precision Instruments, Sarasota, Fla.) with tubing that was connected to a carbon dioxide gas cylinder for application of infusion pressure. The holder was attached to a micromanipulator (KITE, World Precision Instruments) which was used to control insertion of the microneedle into the sclera.

Carboxylate-modified FluoSpheres® (Invitrogen, Carlsbad, Calif.) were injected as 2 wt % solids suspension of 20 nm, 100 nm, 500 nm, and 1000 nm diameter particles. Tween 80 (Sigma-Aldrich, St. Louis, Mo.) at a final concentration of 0.5 wt %, was added to the suspension and sonicated prior to use. Sulforhodamine B (Sigma-Aldrich) was dissolved in Hanks' balanced salt solution (Mediatech, Manassas, Va.) to make a sulforhodmine solution of $10^{-4}$ M. Barium sulfate particles (Fisher Scientific, Waltham, Mass.) measuring 1 µm in diameter were suspended in balanced salt solution (BSS Plus, Alcon, Fort Worth, Tex.) to form a 1.5 wt % suspension.

Figure 7B:
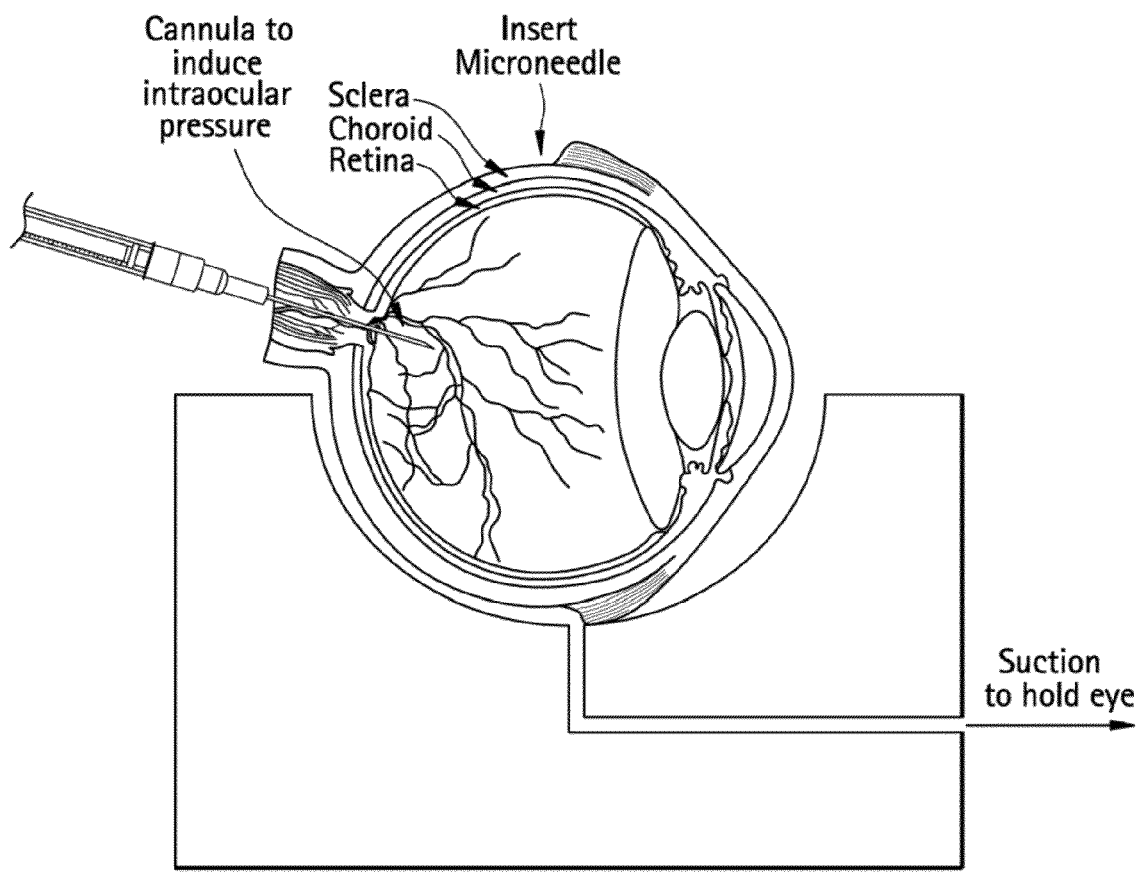
FIG. 7B shows a schematic illustration of a custom acrylic mold shaped to fit a whole eye.

A custom acrylic mold, shaped to fit a whole eye, was built to hold the eye steady and used for all experiments (FIG. 7B). A catheter was inserted through the optic nerve into the vitreous and connected to a bottle of BSS Plus raised to a height to generate internal eye pressure (18 or 36 mm Hg). Suction was applied to a channel within the mold to hold the external surface of the eye steady during microneedle insertion and manipulation. Each microneedle was pre-filled with a desired volume of the material to be injected. The microneedle was placed in the device holder at a set microneedle length, attached to the micromanipulator and connected to the constant pressure source. Microneedles were then inserted perpendicular to the sclera tissue 5-7 mm posterior from the limbus. A set pressure was applied to induce infusion. Thirty seconds were allowed to see if infusion of the solution began. If infusion occurred, the pressure was stopped immediately upon injection of the specified volume. If visual observation of the injected material showed localization in the suprachoroidal space, the injection was considered a success. If infusion had not begun within that timeframe, then the applied pressure was stopped and the needle was retracted. This was considered an unsuccessful delivery.

Eyes to be imaged using microscopy were detached from the set-up within minutes after delivery was completed. The eyes were placed in acetone or isopentane kept on dry ice or liquid nitrogen, causing the eye to freeze completely within minutes after placement. The frozen eye was removed from the liquid and portions of the eye were hand cut using a razor blade for imaging of injected material. Imaging was performed using a stereo microscope using brightfield and fluorescence optics (model SZX12, Olympus America, Center Valley, Pa.). The portions containing the sclera, choroid and retina were placed in Optimal Cutting Temperature media (Sakura Finetek, Torrance, Calif.) and frozen under dry ice or liquid nitrogen. These samples were cryosectioned 10-30 µm thick (Microm Cryo-Star HM 560MV, Walldorf, Germany) and imaged by brightfield and fluorescence microscopy (Nikon E600, Melville, N.Y.) to determine the location of injected material in the eye. Images were collaged as necessary using Adobe Photoshop software (Adobe Systems, San Jose, Calif.).

Pig eyes used for microcomputed tomography imaging were not frozen after injection. Instead, pig eyes were injected with a barium sulfate suspension and stabilized in a 30 mm diameter sample tube and scanned in air using a Scanco µCT40 desktop conebeam system (Scanco Medical AG, Brüttisellen, Switzerland) at 30 µm isotropic voxel size, E=55 kVp, I=145 µA, and integration time=200 ms. Through a convolution backprojection algorithm based on techniques from Feldkamp et. al. (*J. Opt. Soc. Am. A-Opt. Image Sci. Vis.* 1:612-619 (1984)), raw data were automatically reconstructed to generate 2D grayscale tomograms. Global segmentation values (Gauss sigma, Gauss support, and threshold) were chosen for the contrast-enhanced region as well as general eye tissue. Grayscale tomograms were stacked, and 3D binarized images were produced by applying the optimal segmentation values (one image for the entire eye and another for the region injected with contrast agent). These images were overlayed using Scanco image processing language to demonstrate the relative 3D position of the contrast-enhanced region within the entire eye.

Example 1

Figure 8A:
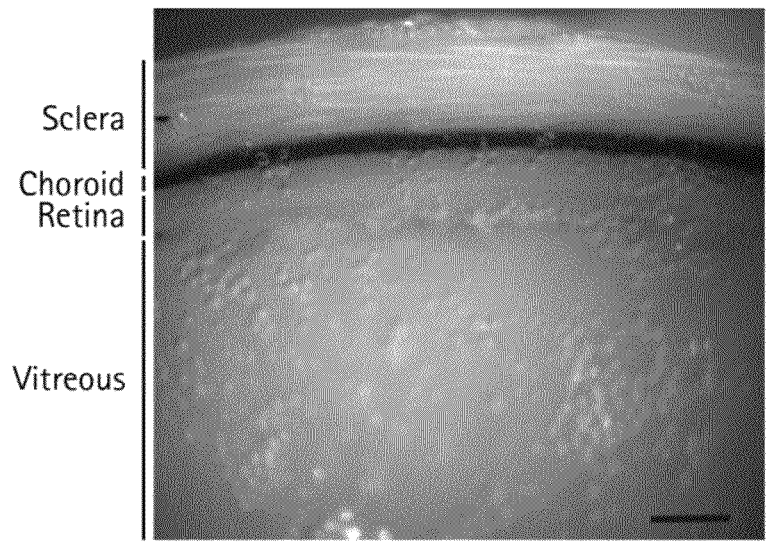
FIGS. 8A and 8B are brightfield microscopic images of saggital cross sections of a pig eye before and after infusion of sulforhadamine, respectively.
Figure 8B:
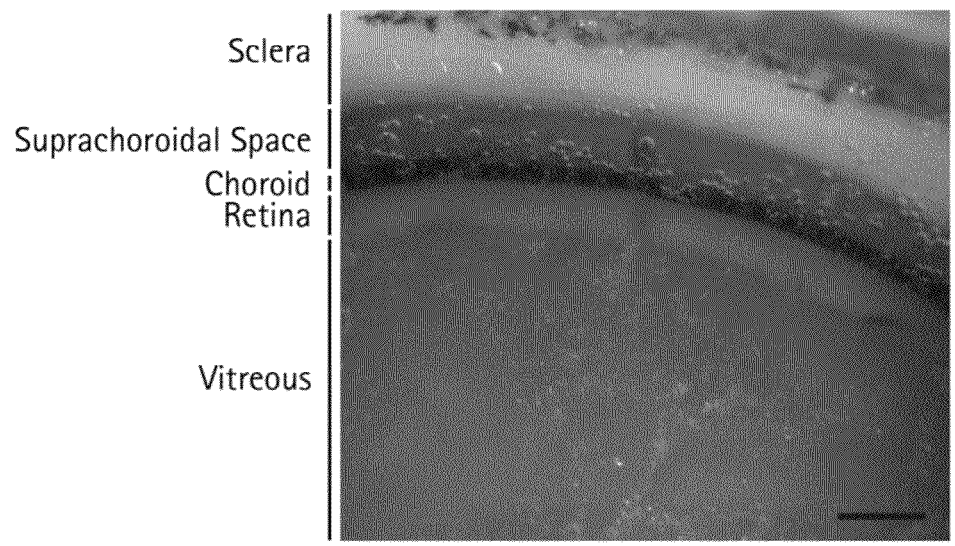

Delivery of a Model Compound to the Suprachoroidal Space Using a Hollow Microneedle Red-fluorescent sulforhodamine B was used as a model compound and injected into pig eyes ex vivo using a single hollow microneedle inserted just to the base of the sclera in order to target the suprachoroidal space. A brightfield microscopic image of the saggital cross section of an untreated pig eye, shown in FIGS. 8A and 8B (Scale bar: 500 µm), was taken both before and after injection of 35 µL of sulforhodamine B. The normal ocular tissue (FIG. 8A) can be distinguished to identify the sclera, choroid, retina, and vitreous humor. After infusion of the model compound (FIG. 8B), the sulforhodamine solution can be seen just below the sclera and above the choroid in the suprachoroidal space, confirming that the solution was injected and spread within the suprachoroidal space from the initial injection site. Volumes up to 35 µL were able to be injected without leakage, but larger volumes leaked out from openings on the surface of the eye where vortex veins would be attached in vivo. However, subsequent experiments in pigs and rabbits in vivo have demonstrated suprachoroidal delivery of up to 100 µL without leakage through these openings (data not shown).

Example 2

Delivery of Particles to the Suprachoroidal Space Using Hollow Microneedles

Figure 9A:
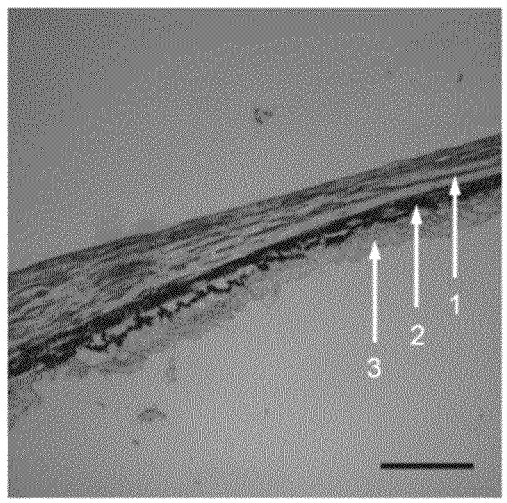
FIGS. 9A, 9B, 9C, and 9D are fluoroscopic images of a cryosection of a pig eye with no infusion into the suprachoroidal space (9A), a cryosection of a rabbit eye after infusion of 500 nm fluorescent particles in the axial plan and collaged to form a panoramic view (9B), a cryosection of a pig eye after infusion of 500 nm fluorescent particles in the saggital direction and collaged to show the spaces both anterior and posterior to the microneedle insertion site (9C), and a cryosection of a human eye after infusion of 500 nm fluorescent particles in the saggital direction and collaged to show spaces both anterior and posterior to the microneedle insertion site (9D). The insets of FIGS. 9B, 9C, and 9D show magnified views of the microneedle insertion site.
Figure 9B:
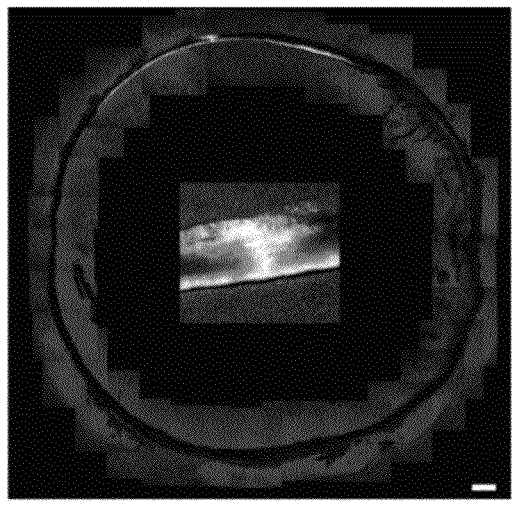

Particles with diameters of 500 nm or 1000 nm were injected into the suprachoroidal space of rabbit, pig and human eyes ex vivo and imaged to evaluate the distribution and localization of the particles just below the sclera. The sclera (1), choroid (2), and retina (3) were identified in a fluoroscopic image of a cryosection of a pig eye with no infusion into the suprachoroidal space (FIG. 9A, Scale bar: 500 µm). Fluoroscopic images of cryosections of a rabbit eye after injection of 500 nm particles were taken in the axial plane and the images were collaged to form a panoramic view (FIG. 9B, Scale bar: 500 µm). The spread of the fluorescent particles (which appear as the bright white regions in the images) was observed along the equator of the eye in a thin sheath just below the sclera. A volume of 15 µL was injected and, in this particular cross-section taken in the plane of the insertion site, the injection had spread approximately 20 mm, which corresponds to about 36% of the total circumference of the eye.

Figure 9C:
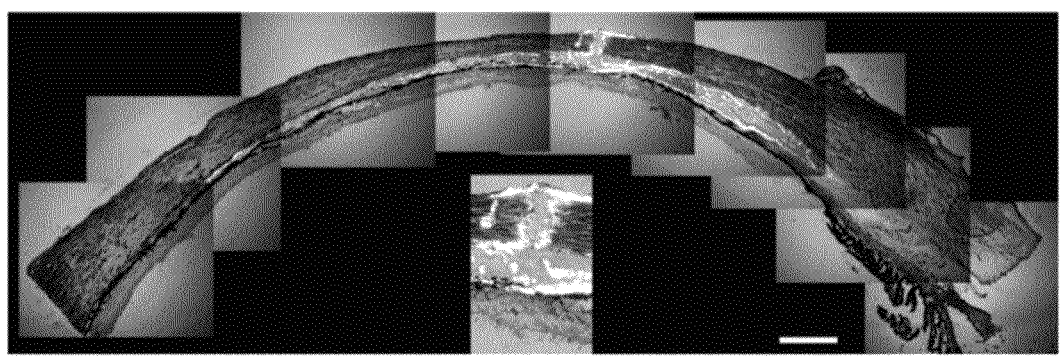
Figure 9D:
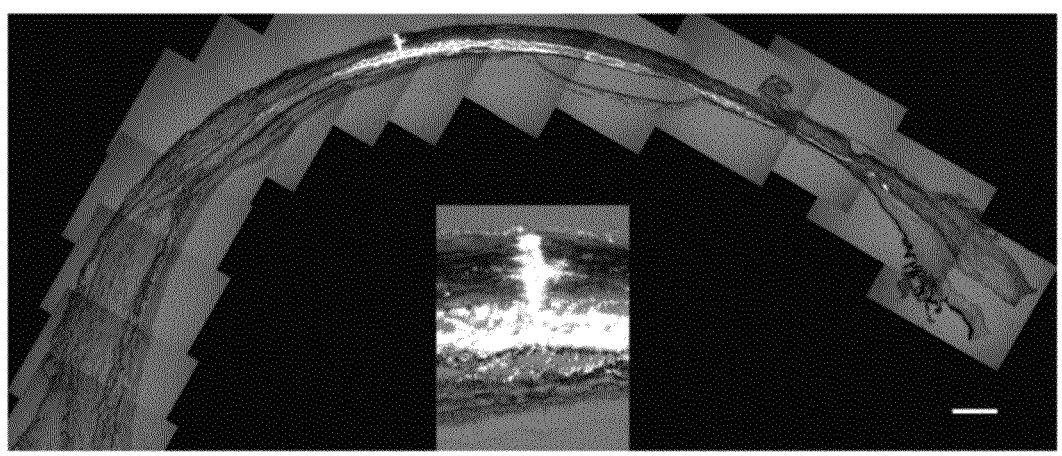

Fluoroscopic images of cryosections of pig and human eyes were taken in the sagittal directions so that the images show the anterior of the eye to the right and the posterior of the eye to the left (FIGS. 9C and 9D, respectively). These images show the ability of microinjected particles (which appear bright white) to spread in the suprachoroidal space both in the anterior and posterior direction of the eye from the injection site. In these experiments, a single microneedle delivered 30 µL of a 2 wt % particle suspension into the suprachoroidal space of both species. Leakage was observed at the vortex vein openings away from the injection site similar to what was observed with sulforhodamine injections.

The insets in these images show magnified views of the microneedle insertion site. In each case, the insertion site within the sclera was filled with particles. In the case of the pig (FIG. 9C) and human (FIG. 9D), the retina was still attached and visible, and it was clear that the microneedle had not penetrated to the retina. In the case of the rabbit (FIG. 9B), the retina separated during the cryosectioning procedure and was not visible. These results confirmed that a microneedle was able to target the suprachoroidal space of rabbit, pig, and human eyes to deliver particles up to 1000 nm in diameter. The results further confirmed that these particles spread from the injection site circumferentially in all directions within the suprachoroidal space.

Figure 10A:
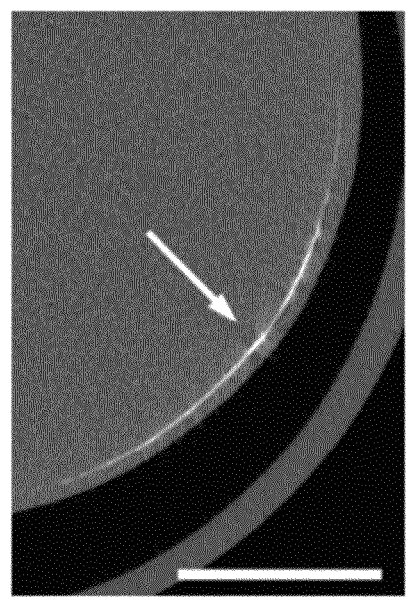
FIGS. 10A and 10B are microcomputed tomography images showing the circumferential spread of 1 μm contrast particles infused into the suprachoroidal space of a pig eye in a cross-sectional image (10A) and a three-dimensional reconstruction of the cross-sectional images (10B).
Figure 10B:
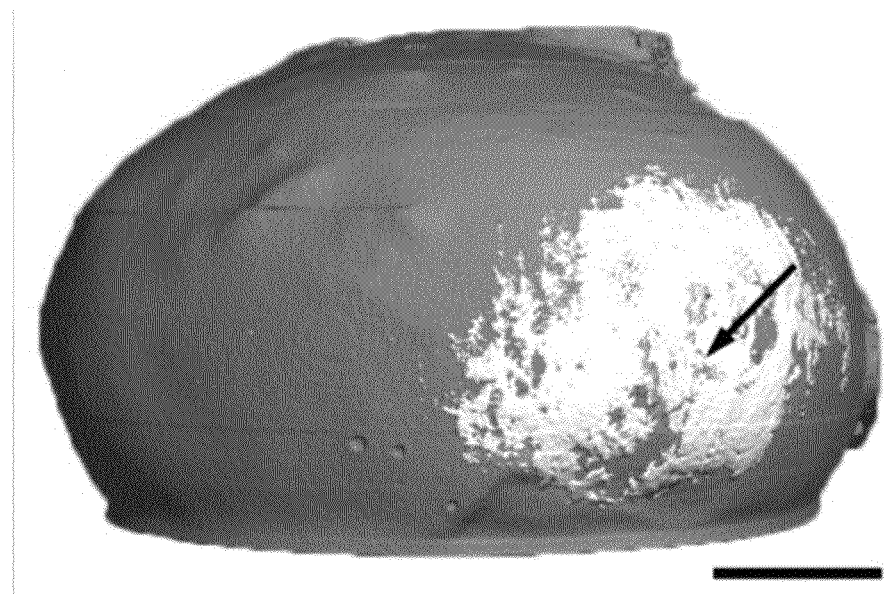

Microcomputed tomography (µCT) was utilized to image the circumferential spread and localization of injected material in the suprachoroidal space in three dimensions using a noninvasive method. After injecting 35 µL of 1 µm diameter barium sulfate contrast agent particles into the suprachoroidal space of a pig eye, cross sectional images showed the particles distributed as a thin white strip that circled just below the outer edge of the eye, i.e., just below the sclera (FIG. 10A). This profile is characteristic of suprachoroidal delivery and similar to the results from fluorescence imaging. The three-dimensional reconstruction of these cross-sectional images showed the spread of the particles in the posterior segment of the eye (FIG. 10B, Scale Bar: 5 mm). The particles spread was approximately 5 mm in radius, although asymmetrically distributed around the injection site, and covered an approximate area of 70 $mm^2$ (which represents 7% of the surface area of the back of the eye). This further confirmed the ability of microneedles to spread particles over a significant portion of the posterior segment of the eye by targeting the suprachoroidal space.

Example 3

Effect of Operating Parameters on Particle Delivery to the Suprachoroidal Space

Particles of 20, 100, 500, and 1000 nm diameter were injected into pig eyes ex vivo using a range of different microneedle lengths and infusion pressures to determine the success rate of suprachoroidal delivery. An attempted injection was considered to be either fully successful (complete injection of the 25 µL particle suspension into the suprachoroidal space) or fully unsuccessful (an inability to inject at all). No partial injections were observed. The effect of infusion pressure and microneedle length on the success rate of suprachoroidal delivery of particles are shown for 20 nm (FIG. 11A), 100 nm (FIG. 11B), 500 nm (FIG. 11C), and 1000 nm (FIG. 11D) particles into pig eyes.

The success rate increased with greater infusion pressure and with greater microneedle length (ANOVA, $p<0.05$). For the 20 nm particles (FIG. 11A), 100% successful injections were achieved using a pressure of 250 kPa at all microneedle lengths. For 100 nm particles (FIG. 11B), the effects of pressure similarly plateaued at 250 kPa and 100% success was achieved at all but the shortest microneedle length (700 μm). For the larger particles (500 and 1000 nm) (FIGS. 11C and 11D, respectively), the effects of pressure generally plateaued at 300 kPa and success rate significantly decreased for shorter microneedles. Not wishing to be bound by any theory, it is believed that short microneedles lengths inject within the sclera, such that particles must be forced through a portion of the sclera to reach the suprachoroidal space. Smaller particles (20 and 100 nm) can more easily force through a portion of the sclera to reach the suprachoroidal space because the spacing of collagen fiber bundles in the sclera is on the order of 300 nm. Larger particles (500 and 1000 nm), however, have more difficulty crossing this anatomical barrier, such that infusion pressure becomes a more important parameter and injection success rate decreases significantly.

A statistical comparison of the injection rates of particles of different sizes at different microneedle lengths was made using ANOVA and is summarized in the following table.

| Microneedle Length | 20 vs 100 nm | 100 vs 500 nm | 500 vs 1000 nm | 20 vs 1000 nm |
|---|---|---|---|---|
| 700 μm | 0.02* | 0.02* | 0.09 | 0.02* |
| 800 μm | 0.37 | 0.00* | 0.10 | 0.01* |
| 900 μm | 0.18 | 0.03* | 0.18 | 0.03* |
| 1000 μm | 0.18 | 0.37 | 0.21 | 0.18 |

Significance was considered to be a $p < 0.05$ and indicated by an asterisk (*).

The statistical analysis showed that at a microneedle length of 700 μm, where the most scleral tissue must be traversed to reach the suprachoroidal space, success rate depended strongly on particle size. Using 800 and 900 μm microneedles, particles smaller than the collagen fiber spacing (20 and 100 nm) behaved similarly and particles larger than the collagen fiber spacing (500 and 1000 nm) also behaved similarly, but there was a significant difference between 100 nm and 500 nm particles. The longest microneedles (1000 μm), which probably reached the base of the sclera, showed no significant dependence on particle size, suggesting that overcoming the collagen barrier in the sclera was no longer needed.

Figure 12A:
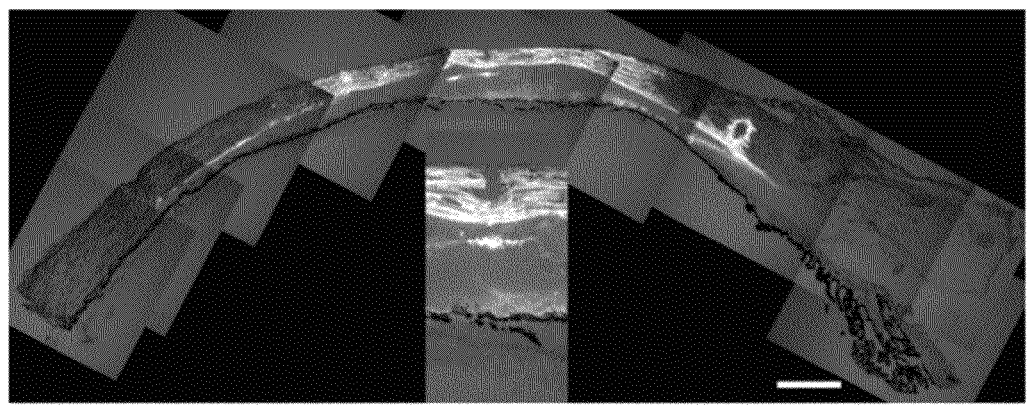
FIGS. 12A and 12B are fluoroscopic images of a cryosection of a pig eye after infusion of 20 nm particles (12A) and 1000 nm particles (12B) in the saggital direction and collaged to show spaces both anterior and posterior to the microneedle insertion site. The insets of FIGS. 12A and 12B show magnified views of the microneedle insertion site.
Figure 12B:
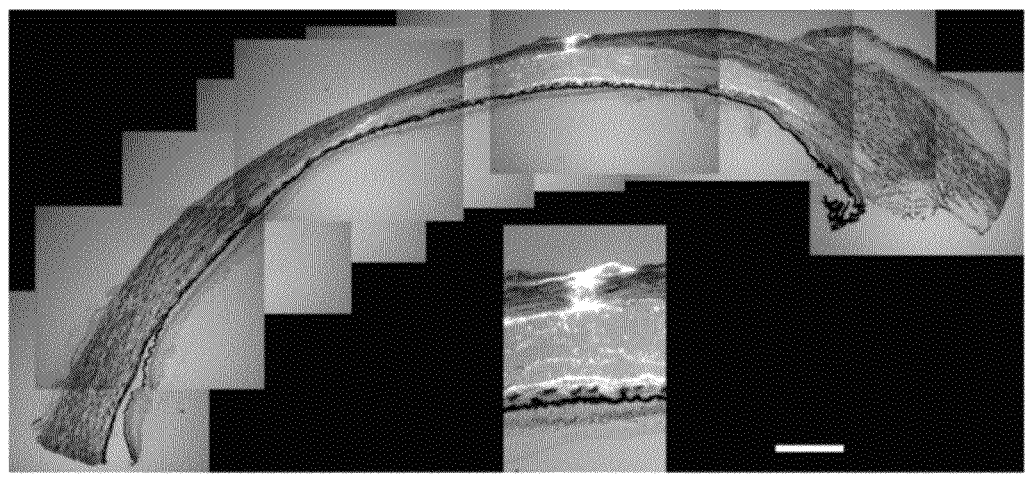

Not wishing to be bound by any particular theory, the foregoing further suggested that particles of 20 and 100 nm can spread within the sclera as well as the suprachoroidal space, whereas particles of 500 and 1000 nm should localize exclusively in the suprachoroidal space. The spread of 20 nm particles (FIG. 12A) was compared to the spread of 1000 nm particles (FIG. 12B) under identical conditions. As expected, the smaller particles exhibited significant spread in the sclera as well as the suprachoroidal space. In contrast, the larger particles were relegated primarily to the suprachoroidal space and were largely excluded from the sclera. This localization of large particles was consistent with the results shown in FIG. 11.

Thus, 20 and 100 nm particles were reliably injected using a minimum microneedle length of 800 μm and a minimum pressure of 250 kPa. To deliver 500 and 1000 nm particles, a minimum microneedle length of 1000 μm and a minimum pressure of 250-300 kPa was required.

Example 4

Figure 13A:
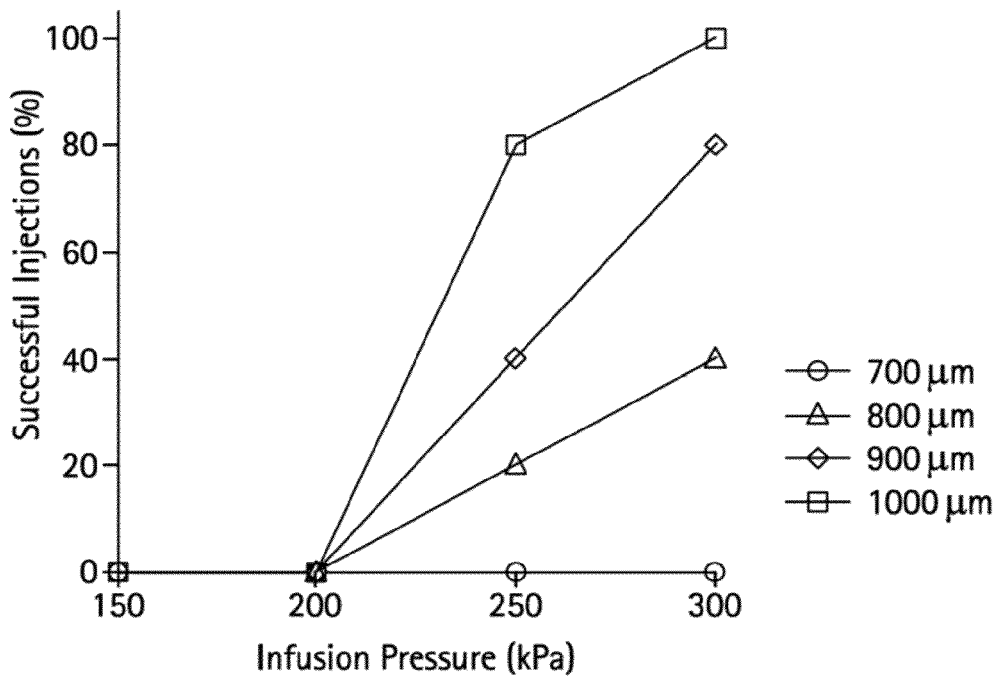
FIGS. 13A and 13B are graphs showing the effect of the intraocular pressure and microneedle length on the success rate of suprachoroidal delivery of 1000 nm particles for a simulated intraocular pressure of 18 mmHg (13A) and 36 mmHg (13B).
Figure 13B:
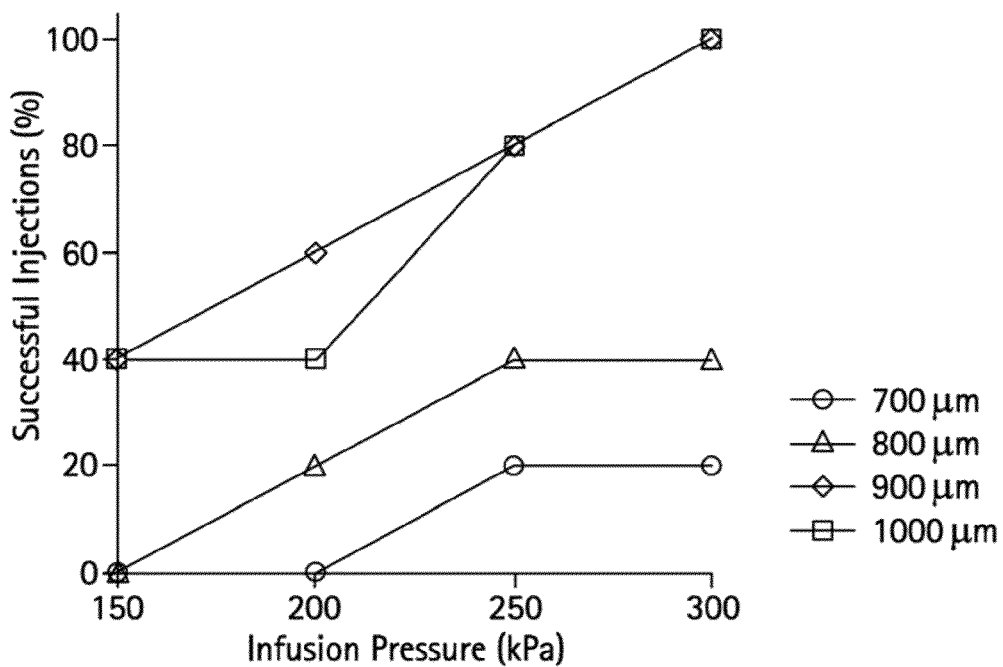

Effect of Intraocular Pressure on Delivery of Particles to the Suprachoroidal Space Intraocular Pressure (IOP) is the internal pressure within the eye that keeps the eye inflated. It provides a back pressure that can counteract the infusion pressure. To evaluate the effect of intraocular pressure on particle delivery to the suprachoroidal space, 1000 nm particles were injected at two different levels of IOP, 18 and 36 mmHg. The effect of infusion pressure and microneedle length on the success rate of suprachoroidal delivery of 1000 nm particles at simulated IOP levels of 18 mmHg and 36 mmHg is shown in FIG. 13A and FIG. 13B, respectively. The delivery success rate generally increased with an increase in IOP. Notably, at normal IOP, no particles were delivered at the lowest infusion pressure (150 kPa) or using the shortest microneedles (700 μm) and only the longest microneedles (1000 μm) achieved 100% success rate at the highest infusion pressure (300 kPa) (FIG. 13A). In contrast, at elevated IOP, particles were sometimes delivered at the lowest infusion pressure and using the shortest microneedles, and a 100% success rate was achieved using both 900 and 1000 μm microneedles at the highest infusion pressure (FIG. 13B).

Not wishing to be bound by any theory, it is believed that the main effect of elevated IOP is to make the sclera surface more firm, reducing tissue surface deflection during microneedle insertion and thereby increasing the depth of penetration into sclera for a microneedle of a given length. Although we did not measure microneedle insertion depth directly, these results suggest that microneedle insertion may be more effective at elevated IOP because they insert deeper into the sclera and thereby increase infusion success rate.

Example 5

Delivery of Model Compound to Suprachoroidal Space in Live Animal Models

Figure 14:
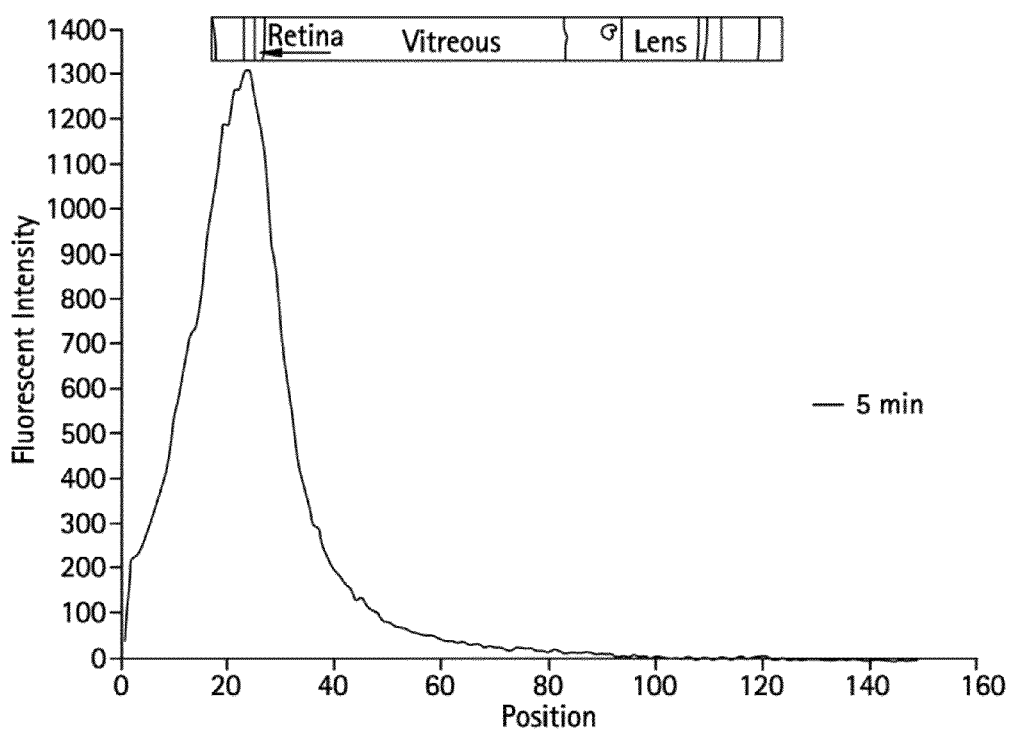
FIG. 14 is a one-dimensional line of sight scan of rabbit eyes taken after injection of sodium fluorescein to the suprachoroidal space, with the x-axis representing the position in the eye from back (0) to front (160) and the y-axis representing the fluorescent intensity at that position.

The delivery of a fluorescent molecule (sodium fluorescein) to the suprachoroidal space was evaluated using rabbits according to approved live animal experimental protocols. A one dimensional scan of the eye (through line of sight) was taken within the first five minutes after injection to determine the dispersion of the fluorescent molecule in the eye (FIG. 14). The y-axis indicates the fluorescent intensity (i.e., the concentration) and the x-axis represents the position in the eye from front (160) to back (0). Thus, the results illustrate that within the first 5 minutes after injection, the fluorescein had already flowed through the suprachoroidal space to the back of the eye, with some remaining at the initial insertion site.

Figure 15:
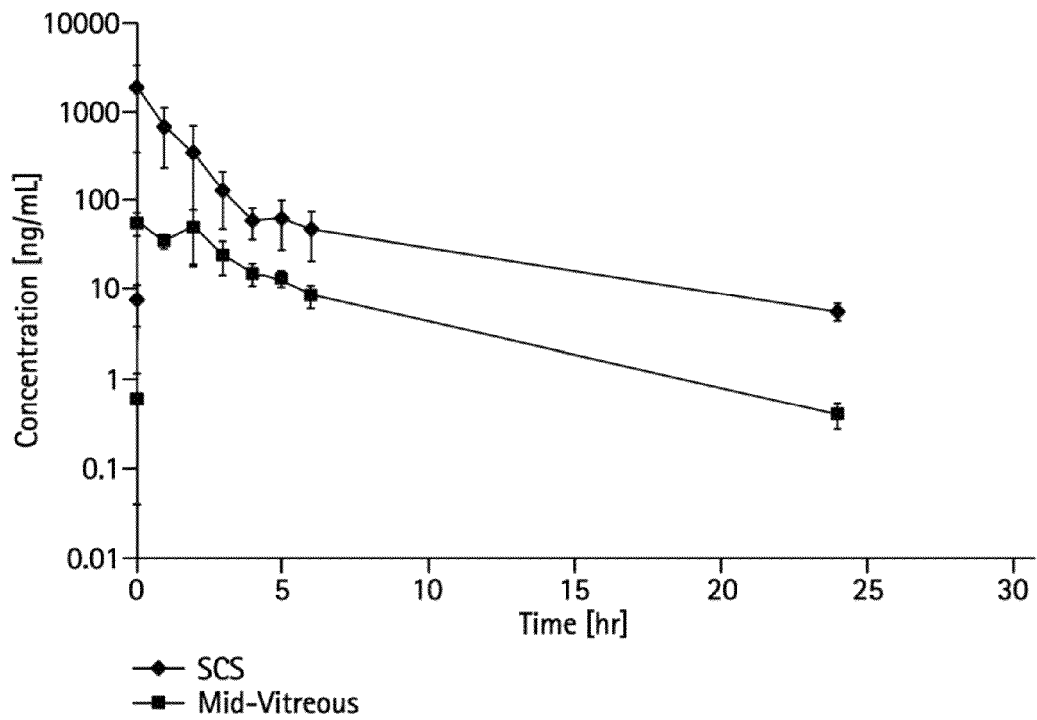
FIG. 15 is a graph showing the rate of clearance of sodium fluorescein from the suprachoroidal space over time.

Similar scans were taken to evaluate the rate of clearance of fluorescein from the suprachoroidal space over time (FIG. 15). The fluorescent intensity was measured in two regions of the eye (the suprachoroidal space and mid-vitreous region) over time. The results illustrate that the bulk of the material injected remains in the suprachoroidal space without passing into the mid-vitreous region and that the material substantially cleared the suprachoroidal space within 24 hours.

Example 6

Delivery of Particles to Suprachoroidal Space in Live Animal Models

Live animal experiments also were conducted to evaluate the delivery of particles to the suprachoroidal space. Fluorescent particles having a diameter of 20 nm and 500 nm were infused into rabbit eyes and the fluorescent intensity was evaluated to determine the length of time the particles remained in two regions of the eye (the suprachoroidal space and mid-vitreous region).

Figure 16:
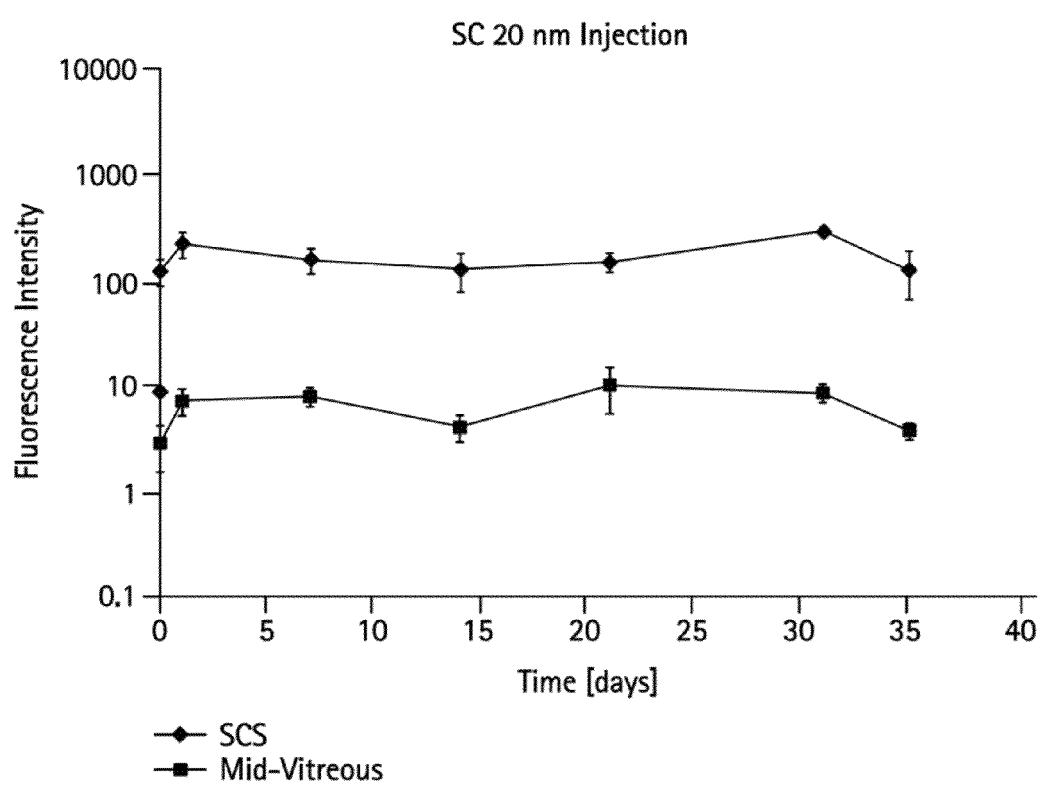
FIG. 16 is a graph showing the rate of clearance of 20 nm particles from the suprachoroidal space over time.
Figure 17:
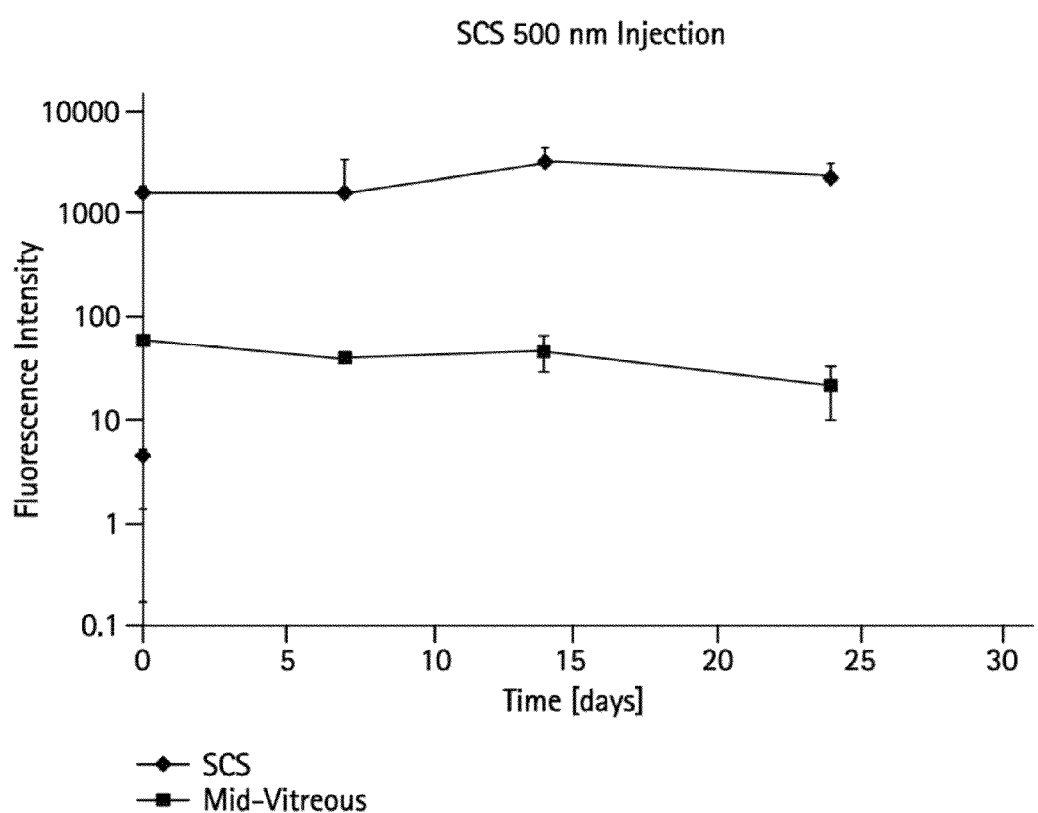
FIG. 17 is a graph showing the rate of clearance of 500 nm particles from the suprachoroidal space over time.

The smaller particles (FIG. 16) were successfully delivered to the suprachoroidal space and remained in the suprachoroidal space for at least 35 days. The larger particles (FIG. 17) also were successfully delivered to the suprachoroidal space and remained in the suprachoroidal space for at least 24 days. Notably, both the smaller and larger particles were well localized as indicated by the low level of fluorescence in the mid-vitreous region.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A method of administering a drug to an eye of a patient, comprising:
   inserting a hollow microneedle into the eye at an insertion site, the microneedle having a tip end with an opening; and
   infusing over a period of time a fluid drug formulation comprising the drug, through the inserted microneedle and into the suprachoroidal space of the eye,
   wherein during the period the infused drug formulation flows within the suprachoroidal space away from the insertion site.

2. The method of claim 1, wherein during the period the infused fluid drug formulation flows at least 5 mm away from the insertion site.

3. The method of claim 1, wherein at least a portion of the fluid drug formulation reaches ocular tissue posterior to the equator of the eye during the period.

4. The method of claim 1, wherein the microneedle is inserted into the surface of the sclera at an angle of about 90 degrees.

5. The method of claim 1, wherein the tip end of the microneedle is inserted substantially to the base of the sclera without completely penetrating through the sclera.

6. The method of claim 1, wherein the tip end of the microneedle is inserted through the sclera into the suprachoroidal space without penetrating through the choroid.

7. The method of claim 1, wherein the fluid drug formulation comprises a suspension of microparticles or nanoparticles, the microparticles or nanoparticles comprising the drug.

8. The method of claim 1, wherein from about 10 μL to about 200 μL of the fluid drug formulation is infused.

9. The method of claim 1, wherein the suspension further comprises a physiologically acceptable aqueous vehicle.

10. The method of claim 1, wherein the fluid drug formulation comprises a formulation that undergoes a phase change after being infused into the suprachoroidal space.

11. The method of claim 1, wherein the step of infusing comprises driving the fluid drug formulation at an infusion pressure of at least 150 kPa.

12. The method of claim 1, wherein the step of infusing comprises driving the fluid drug formulation at an infusion pressure of at least 300 kPa.

13. The method of claim 1, wherein the microneedle has an effective length between 500 microns and 1000 microns.

14. The method of claim 1, wherein the microneedle has an effective length between 700 microns and 1000 microns.

15. The method of claim 1, wherein the microneedle has an effective length between 800 microns and 1000 microns.

16. The method of claim 1, wherein the portion of the microneedle that is inserted into the sclera has a maximum cross-sectional width or diameter of 400 microns.

17. The method of claim 1, wherein the microneedle is formed of metal and has a total effective length between 500 microns and 1000 microns, the microneedle comprising a cylindrical shaft having an outer diameter of between 200 microns and 400 microns, and a beveled tip less than about 400 microns in length.

18. The method of claim 1, wherein the microneedle extends substantially perpendicularly from a planar or convex base.

19. The method of claim 1, wherein the patient is in need of treatment of uveitis, glaucoma, diabetic macular edema, wet or dry age-related macular degeneration, choroidal neovascularization, or cytomegalovirus retinitis.

20. The method of claim 1, wherein the insertion site is at the equator of the eye.

21. The method of claim 1, wherein the insertion site is between the equator and the limbus of the eye.

22. The method of claim 1, wherein from about 10 μL to about 500 μL of the fluid drug formulation is infused.

23. The method of claim 1, wherein the fluid drug formulation flows circumferentially toward the posterior segment of the eye.

24. The method of claim 1, wherein the fluid drug formulation flows posterior to the equator of the eye during the injection.

25. The method of claim 1, wherein the drug comprises an oligonucleotide.

26. The method of claim 25, wherein the oligonucleotide is selected from an antisense oligonucleotide, therapeutic DNA, ribozyme, siRNA, RNAi or double stranded RNA.

27. The method of claim 1, wherein the drug is an antiviral agent.

28. The method of claim 27, wherein the antiviral agent is acyclovir, cidofovir, idoxuridine or an interferon.

29. The method of claim 1, wherein the drug is an analgesic.

30. The method of claim 1, wherein the drug is an anesthetic.

31. The method of claim 1, wherein the drug is a collagenase inhibitor.

32. The method of claim 1, wherein the drug is pegagtanib sodium, ranibizumab or bevacizumab.

33. The method of claim 1, further comprising dissolving a coating of a drug formulation off the hollow microneedle into the eye.

34. The method of claim 1, wherein the fluid drug formulation comprises an anesthetic.

35. The method of claim 33, wherein the coating of the drug formulation comprises an anesthetic.

36. The method of claim 34, wherein the anesthetic is amethocaine, lignocaine, oxbuprocaine or proxymetacaine.

37. The method of claim 35, wherein the anesthetic is amethocaine, lignocaine, oxbuprocaine or proxymetacaine.

38. The method of claim 36, wherein the anesthetic is lignocaine.

39. The method of claim 37, wherein the anesthetic is lignocaine.

* * * * *